US011583520B2

(12) United States Patent
Seifan

(10) Patent No.: US 11,583,520 B2
(45) Date of Patent: Feb. 21, 2023

(54) COMPOSITIONS AND METHODS FOR TREATING NEUROPSYCHIATRIC DISORDERS

(71) Applicant: HB Biotech, Inc., New York, NY (US)

(72) Inventor: Alon Seifan, New York, NY (US)

(73) Assignee: HB Biotech, Inc., New York, NY (US)

( * ) Notice: Subject to any disclaimer, the term of this patent is extended or adjusted under 35 U.S.C. 154(b) by 0 days.

(21) Appl. No.: 17/477,444

(22) Filed: Sep. 16, 2021

(65) Prior Publication Data

US 2022/0023264 A1 Jan. 27, 2022

Related U.S. Application Data

(63) Continuation of application No. PCT/US2021/027641, filed on Apr. 16, 2021.

(60) Provisional application No. 63/111,156, filed on Nov. 9, 2020, provisional application No. 63/011,932, filed on Apr. 17, 2020.

(51) Int. Cl.
| | |
|---|---|
| *A61K 31/4184* | (2006.01) |
| *A61P 25/28* | (2006.01) |
| *A61K 31/277* | (2006.01) |
| *A61K 45/06* | (2006.01) |
| *A61P 25/22* | (2006.01) |

(52) U.S. Cl.
CPC ........ *A61K 31/4184* (2013.01); *A61K 31/277* (2013.01); *A61K 45/06* (2013.01); *A61P 25/22* (2018.01); *A61P 25/28* (2018.01)

(58) Field of Classification Search
CPC .................................................. A61K 31/4184
See application file for complete search history.

(56) References Cited

U.S. PATENT DOCUMENTS

| | | | |
|---|---|---|---|
| 6,548,529 B1 | 4/2003 | Robi et al. | |
| 6,863,901 B2 | 3/2005 | Hirsh et al. | |
| 10,238,749 B2 | 3/2019 | Foster et al. | |
| 10,294,230 B2 | 5/2019 | Shapiro | |
| 10,626,105 B2 | 4/2020 | Zhang | |
| 2011/0269717 A1 | 11/2011 | Barlow et al. | |
| 2015/0098992 A1 | 4/2015 | Kim et al. | |
| 2015/0343067 A1 | 12/2015 | Gemot et al. | |
| 2017/0112875 A1 | 4/2017 | Liu et al. | |
| 2018/0250244 A1 | 9/2018 | Shytle et al. | |
| 2020/0069583 A1 | 3/2020 | Gong et al. | |

FOREIGN PATENT DOCUMENTS

| | | |
|---|---|---|
| CN | 101890165 A | 11/2010 |
| CN | 102266559 A | 12/2011 |
| CN | 109010261 A | 12/2018 |
| WO | 2008141189 A1 | 11/2008 |

OTHER PUBLICATIONS

Albayrak et al., "The Effects of Dual and Triple Combinations of Trandolapril, Telmisartan, and Verapamil on Overt Proteinuria in the Patients with Diabetic Nephropathy," Saudi Journal of Kidney Diseases and Transplantation, May 2016, vol. 27, No. 3, pp. 512-518.
Alzheimer's Drug Discovery Foundation, "Angiotensin II receptor blockers (ARBs)," Cognitive Vitality Reports, Jan. 23, 2019, pp. 1-12.
Behjati, Mohaddeseh, "The concept of Maslow's pyramid for cardiovascular health and its impact on 'change cycle'," ARYA Atherosclerosis, 2014, vol. 10, No. 1, pp. 65-69.
Brownstein et al., "Blockade of the angiotensin system improves mental health domain of quality of life: A meta-analysis of randomized clinical trials," Australian & New Zealand Journal of Psychiatry, 2018, vol. 52, No. 1, pp. 24-38.
Dorosch et al., "Efficacy of Angiotensin-Converting Enzyme Inhibitors and Angiotensin Receptor Blockers in the Preventative Treatment of Episodic Migraine in Adults," Current Pain and Headache Reports, Sep. 12, 2019, vol. 23, Article No. 85, pp. 1-8.
Dorsaint-Pierre et al., "Asymmetries of the planum temporale and Heschl's gyrus: relationship to language lateralization," Brain, 2006, vol. 129, No. 5, pp. 1164-1176.
Ha et al., "Migraine Headache Prophylaxis," American Family Physician, Jan. 1, 2019, vol. 99, No. 1, pp. 17-24.
Huffman et al., "Neuropsychiatric consequences of cardiovascular medications," Dialogues in Clinical Neuroscience, 2007, vol. 9, No. 1, pp. 29-45.
Kalra et al., "Combination therapy in hypertension: An update," Diabetology & Metabolic Syndrome, 2010, vol. 2, Article No. 44, pp. 1-11.
Modi et al., "Medications for Migraine Prophylaxis," American Family Physician, Jan. 1, 2006, vol. 73, No. 1, pp. 72-78.
Pan et al., "Association between anxiety and hypertension: a systematic review and meta-analysis of epidemiological studies," Neuropsychiatric Disease and Treatment, Apr. 22, 2015, vol. 11, pp. 1121-1130.
Pringsheim et al., "Systematic Review: Medications for Migraine Prophylaxis—Section II," The Canadian Journal of Neurological Sciences, 2012, vol. 39, Suppl. 2, pp. S8-S28.
Sareen et al., "Disability and Poor Quality of Life Associated With Comorbid Anxiety Disorders and Physical Conditions," Archives of Internal Medicine, Oct. 23, 2006, vol. 166, No. 19, pp. 2109-2116.
Seifan et al., "Childhood Learning Disabilities and Atypical Dementia: A Retrospective Chart Review," PLoS One, Jun. 24, 2015, vol. 10, No. 6, e0129919, pp. 1-14.
Zheng et al., "Safety Needs Mediate Stressful Events Induced Mental Disorders," Neural Plasticity, 2016, vol. 2016, Article ID 8058093, pp. 1-6.
International Search Report and Written Opinion in corresponding PCT Patent Application No. PCT/US21/27641, dated Jul. 20, 2021 (9 pages).

*Primary Examiner* — Yong S. Chong
(74) *Attorney, Agent, or Firm* — Melissa Hunter-Ensor; Nicholas R. Ballor; Greenberg Traurig, LLP

(57) ABSTRACT

As described below, the present invention features compositions and methods for treating brain and/or behavioral health disorders and their associated symptoms.

19 Claims, 25 Drawing Sheets

COMPOSITIONS AND METHODS FOR TREATING NEUROPSYCHIATRIC DISORDERS

CROSS-REFERENCE TO RELATED APPLICATION

This application is a continuation of PCT Patent Application No. PCT/US21/27641, filed Apr. 16, 2021, which claims the benefit of and priority to U.S. Provisional Application Nos. 63/011,932, filed Apr. 17, 2020, and 63/111,156, filed Nov. 9, 2020, the entire contents of each of which are incorporated herein by reference in their entireties.

BACKGROUND

Brain and behavioral health disorders are the number one cause of disability worldwide. Brain and behavioral health disorders include all of the major disorders that belong to neurology, psychiatry and psychology subspecialties. Anxiety, apathy, cognitive difficulty, depression, fatigue, headache, insomnia, irritability, pain (e.g., body pain), and psychosis are ten cardinal symptoms caused by brain and behavioral health disorders. Individually, these symptoms are disabling features of these disorders, causing loss of function.

All of the ten cardinal symptoms of brain and behavioral health disorders are difficult to treat because most, if not all, people with brain and behavioral disorders suffer from more than one cause of these symptoms. In real clinical practice, the cause of a symptom could be due to neurology, psychiatry, and/or psychological factors. However, patients seek independent treatment for their symptoms. Anxiety, depression, and psychosis are typically treated by a psychiatrist. Headache, pain, and cognitive difficulty is often treated by a neurologist. Irritability, apathy, insomnia and fatigue are often treated by psychologists or primary care doctors. Anxiety is an example of a symptom that is disabling, difficult to treat and multifactorial. Somatic anxiety (hypersensitivity to stimulation) is an example of a neurological cause of anxiety, often related to migraine. Excessive shyness is an example of a psychological cause of anxiety, often related to social phobia. Excessive worry is an example of a psychiatric cause of anxiety, often related to generalized anxiety disorder or obsessive-compulsive disorder.

Despite the fact that the ten cardinal disabling symptoms (i.e., anxiety, apathy, cognitive difficulty, depression, fatigue, headache, insomnia, irritability, pain (e.g., body pain), and psychosis) of brain and behavioral health disorders, in real clinical practice, are multi-factorial, current FDA-approved treatments typically target one component of a disorder at a time. For example, selective serotonin reuptake inhibitors ("SSRI's"), which are the first-line treatment for anxiety disorders, were designed specifically to target serotonergic mechanisms of anxiety. The effectiveness of these medications in and of themselves has proven to be limited. Cognitive behavioral therapy is designed specifically to address psychological components of anxiety. Patients receiving both medication and cognitive behavioral therapy are predicted to have better outcomes than those receiving one targeted treatment or the other. Even with cognitive behavioral therapy and medication, treatment success remains limited, suggesting that neurological underpinnings of anxiety remain untreated in the majority of patients seeking relief for anxiety.

No current treatments have been designed to address the multi-factorial features associated with the most disabling symptoms of brain and behavioral health disorders. Accordingly, new treatments that address brain and behavioral health disorders and their symptoms are urgently needed.

SUMMARY

As described below, the present invention features compositions and methods for treating brain and/or behavioral health disorders and their associated symptoms.

The invention provides novel combination therapies comprising an agent that targets the adrenergic system (e.g., anipamil, devapamil, falipamil, gallopamil, tiapamil, and verapamil) and an agent that targets the renin angiotensin aldosterone system (RAAS) (e.g., candesartan, telmisartan). While such agents have been individually approved by the FDA for the treatment of cardiovascular disease, they have not previously been combined, nor have they been used for the treatment of any brain and/or behavioral health disorder. In an embodiment, the invention provides a combination therapy featuring a first agent selected from one or more of anipamil, devapamil, falipamil, gallopamil, tiapamil, and verapamil and a second agent selected from one or more of candesartan and telmisartan. Without intending to be bound by theory, the combinations provided herein create novel, synergistic, equilibrating effects on whole brain cerebral blood flow via modulation of stress-induced hormones in both the body and brain.

These combinations are effective in treating brain and/or behavioral health disorders, and their associated symptoms, including but not limited to anxiety, apathy, cognitive difficulty, depression, fatigue, headache, insomnia, irritability, pain (e.g., body pain), and psychosis.

In one aspect, the invention features a therapeutic combination for the treatment of a brain and/or behavioral health disorder or symptom thereof. The combination contains an effective amount of a first agent that targets the adrenergic system and an effective amount of a second agent that targets the renin angiotensin aldosterone system.

In another aspect, the invention features a therapeutic combination for the treatment of anxiety disorder containing an effective amount of a first and a second agent. The first agent is verapamil and the second agent is telmisartan, and the first and second agents are provided in an extended release formulation.

In another aspect, the invention features a method for treating a subject having a brain or behavioral health disorder. The method involves administering to the subject a combination therapy containing a first agent that targets the adrenergic system and a second agent that targets the renin angiotensin aldosterone system, thereby treating the brain or behavioral health disorder.

In another aspect, the invention features a method for treating an anxiety disorder involving administering to a subject a therapeutic combination containing effective amounts of a first and a second agent. The first agent is verapamil and the second agent is telmisartan. The first and second agents are provided in an extended release formulation.

In another aspect, the invention features a method of increasing advancement of a subject along Maslow's hierarchy of needs. The method involves administering to the subject a therapeutically effective amount of a first agent and of a second agent. The first agent alters metabolism and/or blood flow associated with the adrenergic system and the second agent alters metabolism and/or blood flow associated with the brain renin angiotensin aldosterone system, thereby increasing advancement of the subject along Maslow's hierarchy of needs. The increase in advancement is relative to a reference.

In one aspect, the invention features a pharmaceutical composition containing effective amounts of a first and second agent and a pharmaceutically acceptable excipient. The first agent is selected from one or more of anipamil, devapamil, falipamil, gallopamil, tiapamil, and verapamil and the second agent is selected from one or more of telmisartan and candesartan. In embodiments, the pharmaceutical composition further contains magnesium oxide.

In another aspect, the invention features a kit containing a therapeutic combination containing a therapeutic combination containing a first and second agent. The first agent is selected from one or more of anipamil, devapamil, falipamil, gallopamil, tiapamil, and verapamil and the second agent is selected from one or more of telmisartan and candesartan. The kit also contains instructions for the use of the combination for the treatment of a brain and/or behavioral health disorder or a symptom thereof.

In any of the above aspects, the first agent has calcium channel blocking activity and the second agent has angiotensin II receptor blocking activity. In any of the above aspects, the first agent is selected from one or more of anipamil, devapamil, falipamil, gallopamil, tiapamil, and verapamil. In any of the above aspects, the first agent is verapamil. In any of the above aspects, the second agent is telmisartan or candesartan. In any of the above aspects, the second agent is telmisartan. In any of the above aspects, the second agent is candesartan.

In any of the above aspects, the combination is labeled for the treatment of a brain and/or behavioral health disorder. In any of the above aspects, the combination is labeled for the treatment of a symptom of a brain and/or behavioral health disorder selected from one or more of anxiety, apathy, cognitive difficulty, depression, fatigue, headache, insomnia, irritability, pain and psychosis.

In any of the above aspects, the effective amount of the first agent is from about 120 mg to about 720 mg and the effective amount of the second agent is from about 45 mg to about 180 mg. In any of the above aspects, the effective amount of the first agent is about 288 mg and the effective amount of the second agent is about 96 mg.

In any of the above aspects, the mass ratio of the first agent to the second agent is from about 2:1 to about 5:1. In any of the above aspects, the mass ratio of the first agent to the second agent is about 2:1. In any of the above aspects, the amount of first agent is from about 1 to about 4 times the amount of the second agent. In any of the above aspects, the amount of first agent is from about 1 to about 4 times the amount of the second agent.

In any of the above aspects, the agents are formulated together or separately.

In any of the above aspects, the combination therapeutic is administered once daily. In any of the above aspects, the combination therapeutic is administered twice daily.

In any of the above aspects, the agents are administered simultaneously. In any of the above aspects, the agents are administered sequentially.

In any of the above aspects, the administration is associated with an alteration in cerebral metabolism or cerebral blood flow. In embodiments, cerebral blood flow is altered in one or more of the telencephalon, the diencephalon, and the mesencephalon. In embodiments, the alteration in regional cerebral blood flow is associated with the establishment of hemodynamic equilibrium in a region of the brain.

In any of the above aspects, the method increases a primary outcome selected from one or more of cognitive function, life satisfaction, the subject's sense of meaning and purpose, the subject's sense of emotional or instrumental support, friendship, and life satisfaction.

In any of the above aspects, the therapeutic combination further containing magnesium oxide. In any of the above aspects, the therapeutic combination contains at least about 150 mg magnesium oxide. In any of the above aspects, the method further involves administering magnesium oxide to the subject. In embodiments, at least about 150 mg magnesium oxide is administered to the subject daily.

Other features and advantages of the presently disclosed embodiments will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "agent" is meant any small molecule chemical compound. Exemplary agents include but are not limited to anipamil, candesartan, devapamil, falipamil, gallopamil, telmisartan, tiapamil, and verapamil.

By "ameliorate" is meant decrease, suppress, attenuate, diminish, arrest, or stabilize the development or progression of a disease.

By "alteration" is meant a positive or negative change. As used herein, an alteration includes a 5%, 10%, 15%, 20%, 25%, 30%, 35%, 45%, 50%, 55%, 60%, 65%, 70%, 75%, 80%, 85%, 90%, 95%, or 100% change. The change can be an increase or a reduction. The measured quantity can be an amount of regional cerebral blood flow. The measured quantity can be a quantitative assessment of the magnitude of a symptom of a disease (e.g., anxiety, apathy, cognitive difficulty, depression, fatigue, headache, insomnia, irritability, pain (e.g., body pain), or psychosis). In some embodiments, an alteration is a reduction in a symptom associated with a brain and/or behavioral health disorder. In some embodiments, an alteration is an increase in function associated with the treatment of a brain and/or behavioral health disorder.

By "ameliorate" is meant decrease, suppress, attenuate, diminish, arrest, or stabilize the development or progression of a disease.

By "analog" is meant a molecule that is not identical to a molecule of interest, but that has analogous functional and/or structural features. In some embodiments, an analog is an agent that targets the adrenergic system. In some embodiments, an analog is an agent that targets the renin angiotensin aldosterone system.

By "anipamil" is meant a compound having the following structure:

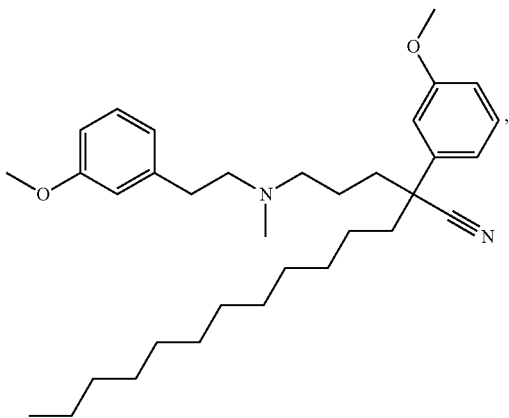 [SMILES: CCCCCCCCCCCCC(C#N)(CCCN(C)CCc1cccc(OC)c1)c1cccc(OC)c1]

or a pharmaceutically acceptable salt thereof. In some embodiments, anipamil has calcium channel blocking activity.

By "candesartan" is meant a compound having the following structure:

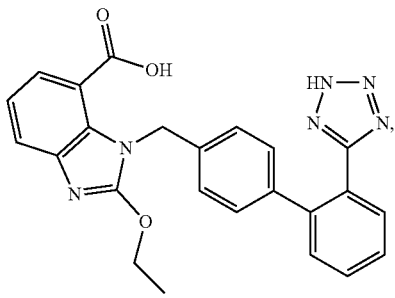 [SMILES: CCOc1nc2cccc(C(=O)O)c2n1Cc1ccc(-c2ccccc2-c2nn[nH]n2)cc1]

or a pharmaceutically acceptable salt thereof. In some embodiments, candesartan has angiotensin II receptor blocking activity.

By "cerebral metabolism" is meant the rate of metabolism in the brain or a region thereof. Cerebral metabolism is measured using any of a variety of methods available to a practitioner including, as non-limiting examples thereof, X-ray computed tomography (CT), positron emission tomography (PET), near-infrared spectroscopy (NIRS), magnetic resonance imaging (MRI), and those methods provided herein. In embodiments, an increase in metabolism in a region of the brain is associated with an increase in blood flow to the region. Cerebral blood flow is measured using any of a variety of methods available to a practitioner including, as non-limiting examples thereof, single-photon emission computed tomography (SPECT), positron emission tomography (PET), functional MRI (fMRI), arterial spin labeling (ASL) MRI, transcranial Doppler ultrasound imaging (i.e., sonography), phase-contrast MRI, and near-infrared spectroscopy (NIRS).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. Any embodiments specified as "comprising" a particular component(s) or element(s) are also contemplated as "consisting of" or "consisting essentially of" the particular component(s) or element(s) in some embodiments.

By "consist essentially" it is meant that the ingredients include only the listed components along with the normal impurities present in commercial materials and with any other additives present at levels which do not affect the operation of the disclosure, for instance at levels less than 5% by weight or less than 1% or even 0.5% by weight.

By "decrease" is meant a negative alteration.

By "devapamil" is meant a compound having the following structure:

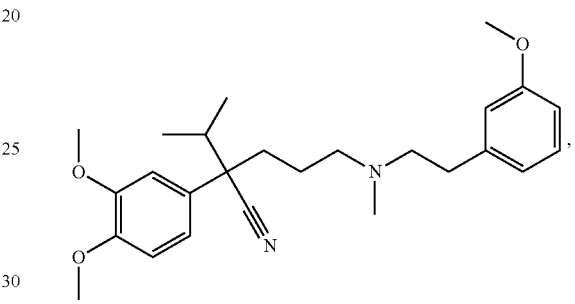

or a pharmaceutically acceptable salt thereof. In an embodiment, devapamil has calcium channel blocking activity.

By "disease" is meant any condition or disorder that damages or interferes with the normal function of a cell, tissue, or organ. In embodiments, the disease or disorder is a neuropsychiatric disorder, examples of which include brain and/or behavioral health disorders and symptoms thereof. Non-limiting examples of brain and behavioral health disorders include affective disorders, anxiety disorders, neurodegenerative disorders, neurodevelopmental disorders, psychotic disorders, personality disorders, migraine disorders and somatoform disorders. Examples of affective disorders include bipolar disorder, cyclothymia, depression, dysthemia, generalized anxiety disorder, major depressive disorder, obsessive compulsive disorder, postpartum depression, post-traumatic stress disorder (PTSD), phobias, and seasonal affective disorder. Examples of anxiety disorders include panic disorder, social anxiety disorder, post-traumatic stress disorder, obsessive compulsive disorder, and specific phobia. Examples of neurodegenerative disorders include Alzheimer's disease and Parkinson's disease. Examples of neurodevelopmental disorders include autism spectrum disorder, attention deficit hyperactive disorder (ADHD) and learning disorders. Examples of psychotic disorders include schizophrenia, schizoaffective disorder, and major depression with psychosis. Examples of personality disorders include paranoid, schizoid, schizotypal, antisocial, borderline, histrionic, narcissistic, avoidant, dependent, and obsessive-compulsive personality disorder. Examples of migraine-related disorders include migraine with aura, migraine without aura, acephalgic migraine, and basilar migraine. Examples of somatoform disorders include somatization disorder, hypochondriasis, conversion disorder, body dysmorphic disorder and chronic pain. The symptoms associated with the disease are selected from one or more of the "ten cardinal symptoms" associated with brain and behavioral health disorders, including but not limited to anxiety, apathy, cognitive difficulty, depression, fatigue, headache, insomnia, irritability, pain (e.g., body pain), and psychosis. In embodiments, the disease is associated with altered regional cerebral blood flow relative to a reference (e.g., the blood flow present in a healthy control brain). the disease can be a brain or behavioral health disorder as defined above.

By "effective amount" is meant an amount of an agent sufficient to treat a disease or disorder. In one embodiment, an effective amount of a combination therapy described herein is sufficient to treat a brain and/or behavioral disorder or a symptom thereof, or to effect an improvement in a primary outcome (e.g., increase cognitive function, life satisfaction, the subject's sense of meaning and purpose, the subject's sense of emotional or instrumental support, friendship, and life satisfaction).

By "falipamil" is meant a compound having the following structure:

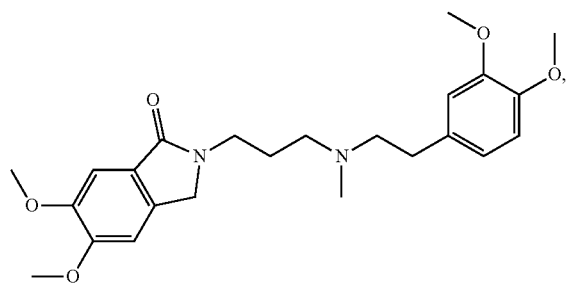

or a pharmaceutically acceptable salt thereof. In some embodiments, falipamil has calcium channel blocking activity.

By "gallopamil" is meant a compound having the following structure:

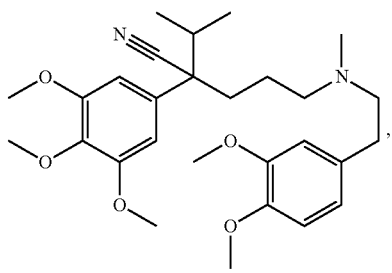 [SMILES: COc1ccc(CCN(C)CCCC(C#N)(c2cc(OC)c(OC)c(OC)c2)C(C)C)cc1OC]

or a pharmaceutically acceptable salt thereof. In some embodiments, gallopamil has calcium channel blocking activity.

By "hemodynamic equilibrium" is meant a state of balance with respect to relative blood flow rates among corresponding regions of the brain. In embodiments, hemodynamic equilibrium is associated with approximately equal relative blood flow rates and/or metabolic activity among the regions.

By "increases" is meant a positive alteration.

As used herein, "obtaining" as in "obtaining an agent" includes synthesizing, purchasing, or otherwise acquiring the agent.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reduces" is meant a negative alteration.

By "subject" is meant a mammal. Non-limiting examples of mammals include a human or non-human mammal, such as a bovine, equine, canine, ovine, feline, or rodent.

By "reference" is meant a standard or control condition. In one embodiment, the effect of an agent on a cell is compared to the effect of the agent on a control cell. In embodiments, the reference is a healthy subject. In embodiments, a clinical feature of subject having a brain or behavioral disorder is compared to a reference clinical feature present in a healthy subject. The healthy subject is a subject not having a disorder or condition of interest. In some embodiments, the reference is an untreated patient or a subject prior to treatment or prior to an alteration in treatment.

By "region of the brain" is meant a portion of the brain. In embodiments, the portion of the brain contains one or more of the telencephalon, the diencephalon, and the mesencephalon. The region can contain all three of the telencephalon, the diencephalon, and the mesencephalon.

By "simultaneous administration" is meant administering concurrently.

By "sequential administration" is meant administered at separate points in time. For example, one or more agents are administered sequentially if the administration is separated by minutes, hours, or days. For example, in sequential administration a first agent is administered 15, 30, 45, or 60 minutes prior to the administration of one or more additional agents. In another example of sequential administration, a first agent is administered 1, 2, 3, 4, 5, 6, 12, or 24 hours prior to the administration of the second agent. In yet another example of sequential administration, a first agent is administered 1, 2, 3, 4, 5, 6, or 7 days prior to the administration of the second agent.

By "telmisartan" is meant a compound having the following structure:

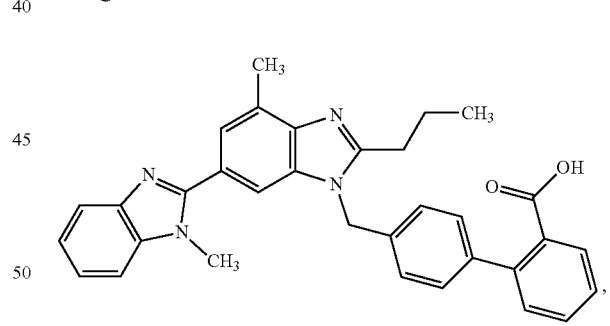

or a pharmaceutically acceptable salt thereof. In some embodiments, telmisartan has angiotensin II receptor blocking activity.

"Therapeutic agent" means a substance that has the potential of affecting the function of an organism. Such a compound is, for example, a naturally occurring, semi-synthetic, or synthetic agent. For example, an agent is a drug that targets a specific function of an organism. A therapeutic agent can decrease, suppress, attenuate, diminish, arrest, or stabilize the development or progression of disease, disorder, or condition. A therapeutic agent is associated with an alteration in regional cerebral blood flow in a subject. Non-limiting examples of therapeutic agents described herein include anipamil, candesartan, devapamil, falipamil, gallopamil, telmisartan, tiapamil, and verapamil, as well as derivatives, analogs, and functional equivalents of such agents. In embodiments, a therapeutic combination features a first agent selected from one or more of anipamil, devapamil, falipamil, gallopamil, tiapamil, and verapamil and a second agent selected from one or more of candesartan and telmisartan.

By "effective amount" is meant the amount of an agent required to reduce or ameliorate a symptom of a disease relative to a reference. The effective amount of active compound(s) (e.g., anipamil, candesartan, devapamil, falipamil, gallopamil, telmisartan, tiapamil, and verapamil) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. The symptom is selected from one or more of "ten cardinal symptoms" associated with brain and behavioral health disorders: anxiety, apathy, cognitive difficulty, depression, fatigue, headache, insomnia, irritability, pain (e.g., body pain), and psychosis. In embodiments, the therapeutically effective amount is the amount of an agent or combination of agents necessary Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "tiapamil" is meant a compound having the following structure:

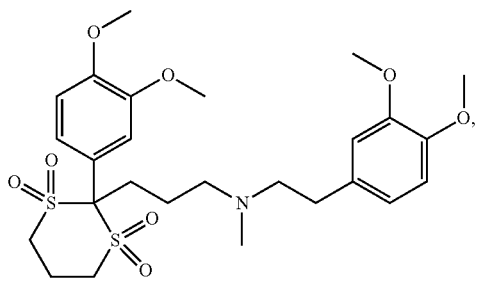 [SMILES: COc1ccc(CCN(C)CCCC2(c3ccc(OC)c(OC)c3)S(=O)(=O)CCCS2(=O)=O)cc1OC]

or a pharmaceutically acceptable salt thereof. In some embodiments, tiapamil has calcium channel blocking activity.

As used herein, the terms "treat," "treating," "treatment," and the like refer to reducing or ameliorating a disease and/or symptoms associated therewith. It will be appreciated that, although not precluded, treating a disorder or condition does not require that the disorder, condition or symptoms associated therewith be completely eliminated.

By "verapamil" is meant an agent having the following structure:

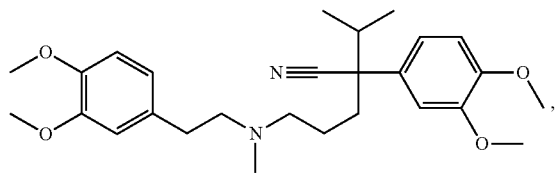

or a pharmaceutically acceptable salt thereof. In some embodiments, verapamil has calcium channel blocking activity.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein. Where various mechanisms of action, hypotheses, or theories are discussed throughout the application, these are not intended to be limiting.

BRIEF DESCRIPTION OF THE DRAWINGS

FIG. 1A is a graph showing lower overall symptomatology between patients on vs. off the combination therapy. FIG. 1B is a graph showing lower self-reported anxiety in patients on vs. off the combination therapy. FIG. 1C is a graph showing lower self-reported depression in patients on vs. off the combination therapy. FIG. 1D is a graph showing lower self-reported irritability in patients on vs. off the combination therapy. FIG. 1E is a graph showing lower self-reported apathy in patients on vs. off the combination therapy. FIG. 1F is a graph showing lower self-reported fatigue in patients on vs. off the combination therapy. FIG. 1G is a graph showing lower self-reported body pain in patients on vs. off the combination therapy. FIG. 1H is a graph showing less severe self-reported insomnia severity in patients on vs. off the combination therapy. FIG. 1I is a graph showing decrease in self-reported headache in patients on vs. off the combination therapy. FIG. 1J is a graph showing a decrease in self-reported cognitive difficulty in patients on vs. off the combination therapy.

FIG. 2A is a graph showing higher general life satisfaction in patients on vs. off combination therapy. FIG. 2B is a graph showing greater meaning and purpose in patients on vs. off combination therapy. FIG. 2C is a graph showing higher emotional support in patients on vs. off treatment with combination therapy. FIG. 2D is a graph showing higher instrumental support in patients on vs. off treatment with combination therapy. FIG. 2E is a graph showing higher friendship in patients on vs. off treatment with combination therapy. FIG. 2F is a graph showing lower loneliness in between patients on vs. off combination therapy.

FIG. 3A is a graph showing the difference in life satisfaction as measured by the NIH Toolbox between patients receiving the combination therapy and patients receiving telmisartan only. FIG. 3B is a graph showing the difference in anger (hostility) as measured by the NIH Toolbox between patients receiving the combination therapy and patients receiving telmisartan only.

FIG. 4A is a graph showing the difference in self-efficacy as measured by the NIH Toolbox between patients receiving the combination therapy and patients receiving telmisartan only. FIG. 4B is a graph showing the difference in anger (aggression) as measured by the NIH Toolbox between patients receiving the combination therapy and patients receiving verapamil only.

DETAILED DESCRIPTION

Figure 1A:
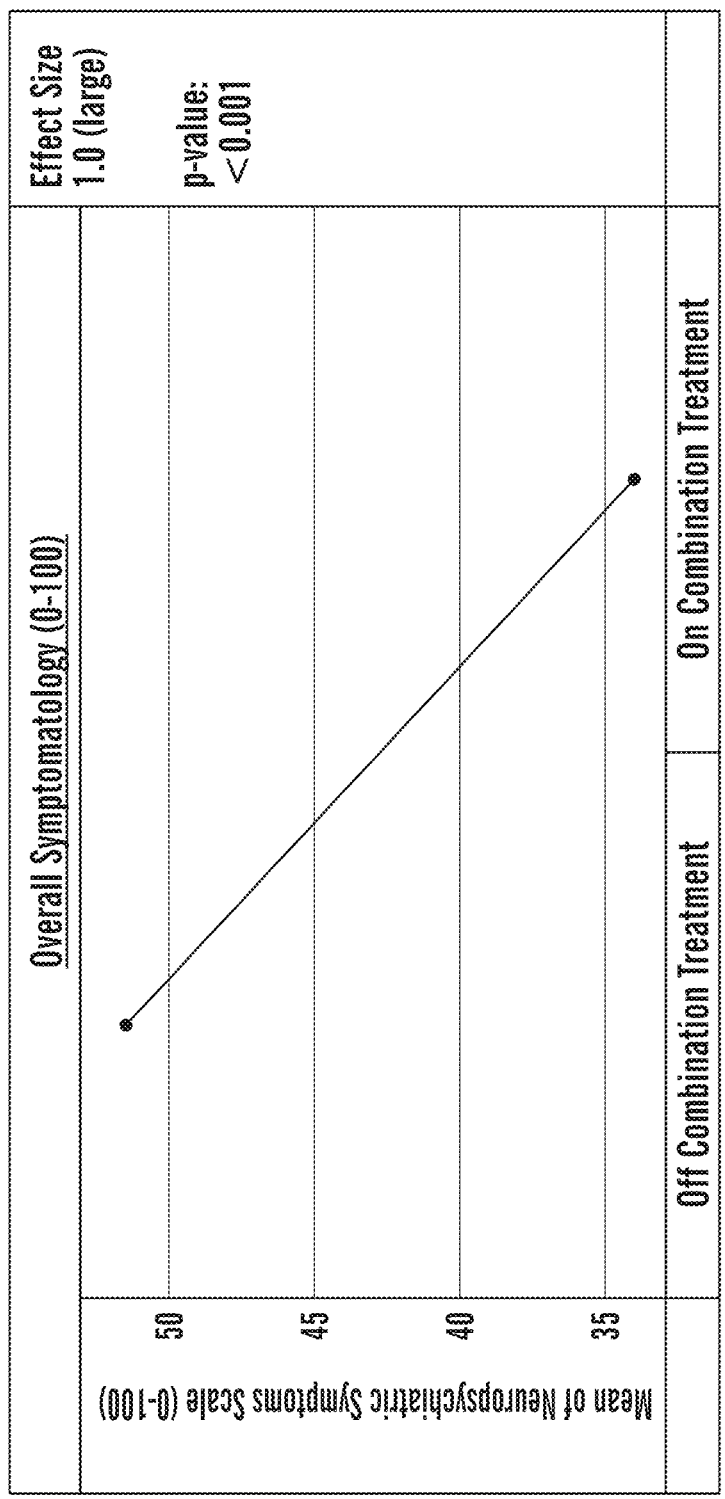
FIGS. 1A-1J are graphs illustrating differences in symptoms in 76 patients before vs. after combination therapy with telmisartan and verapamil. Combination therapy comprised either 120 mg or 180 mg of verapamil twice per day with either 40 mg or 80 mg of telmisartan twice per day.
Figure 1B:
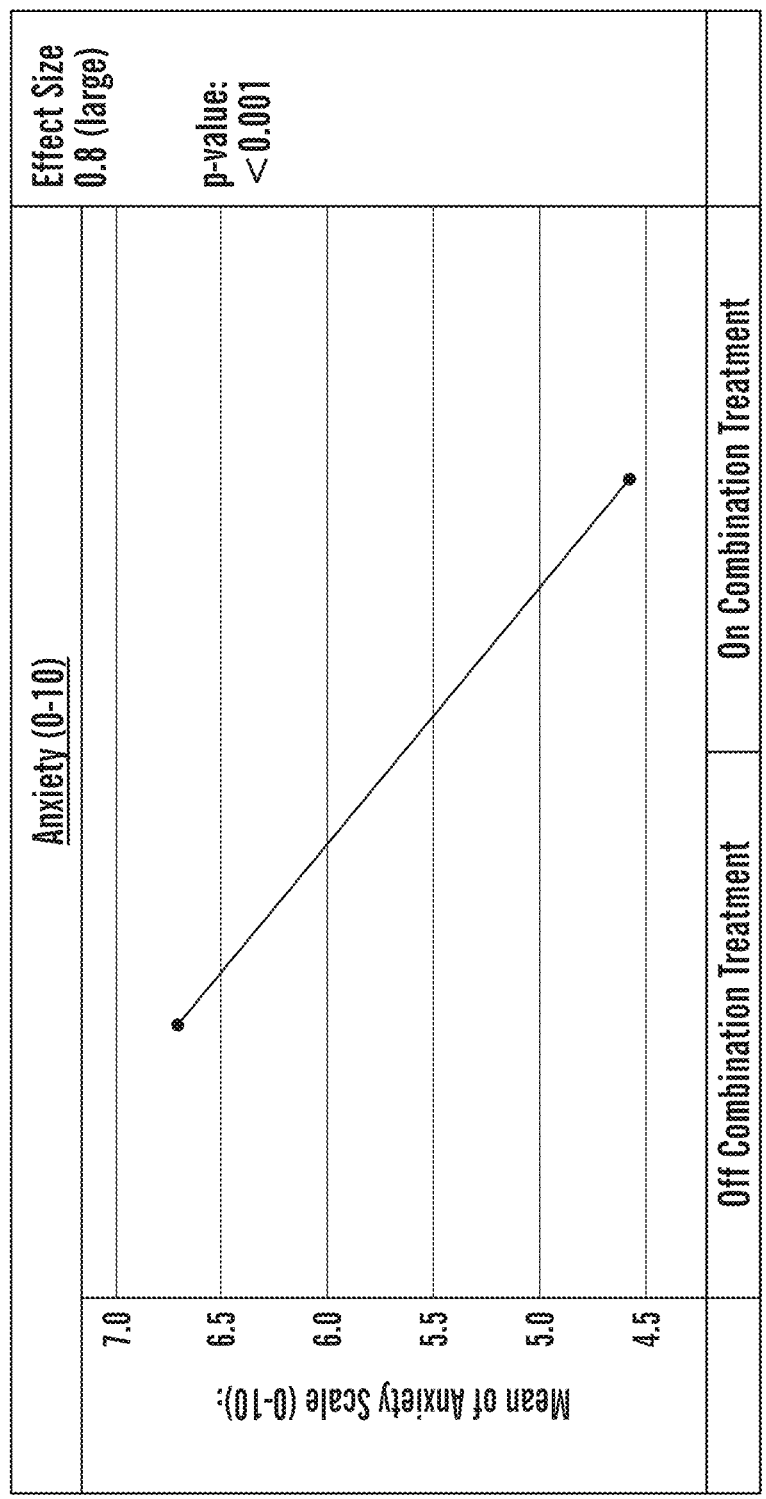
Figure 1C:
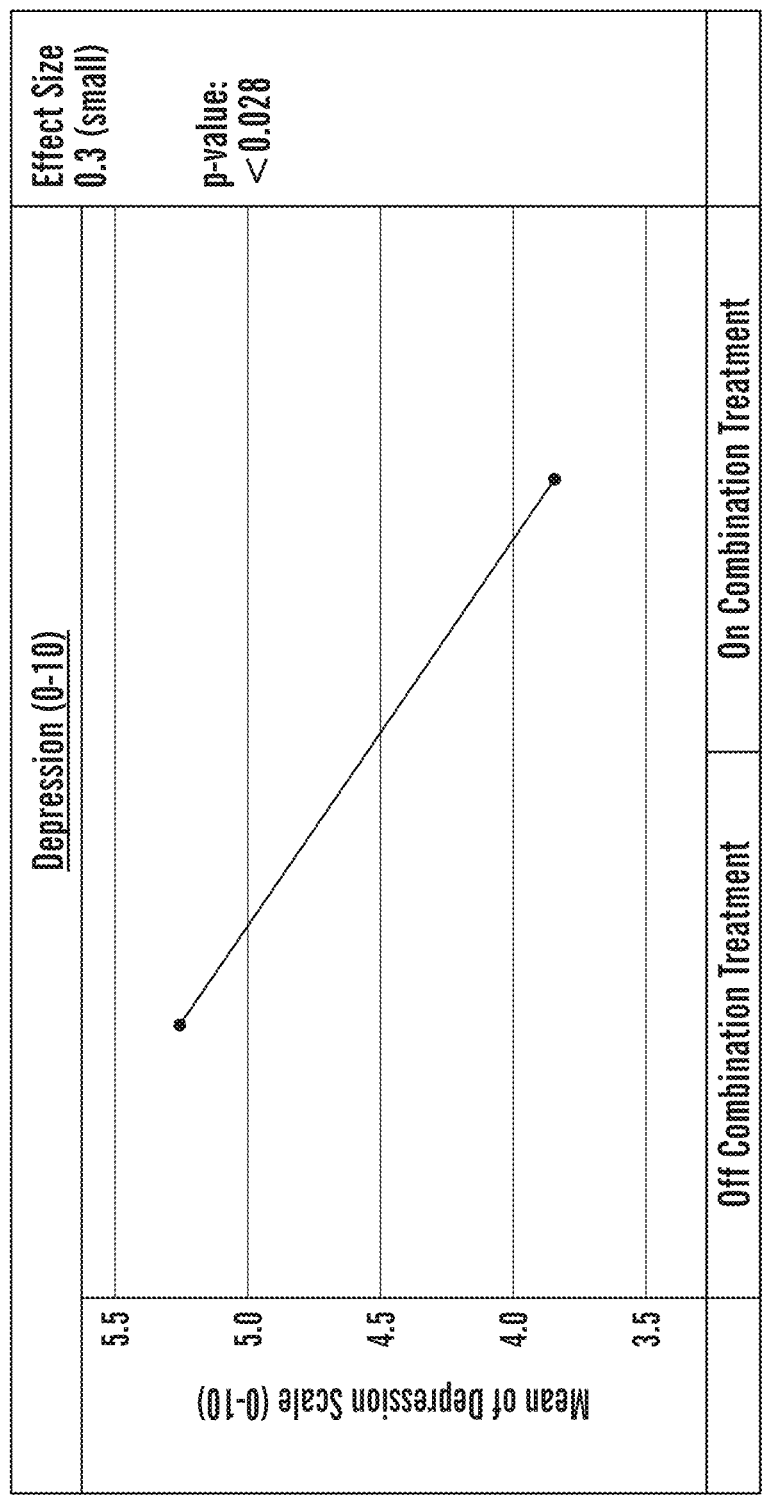
Figure 1D:
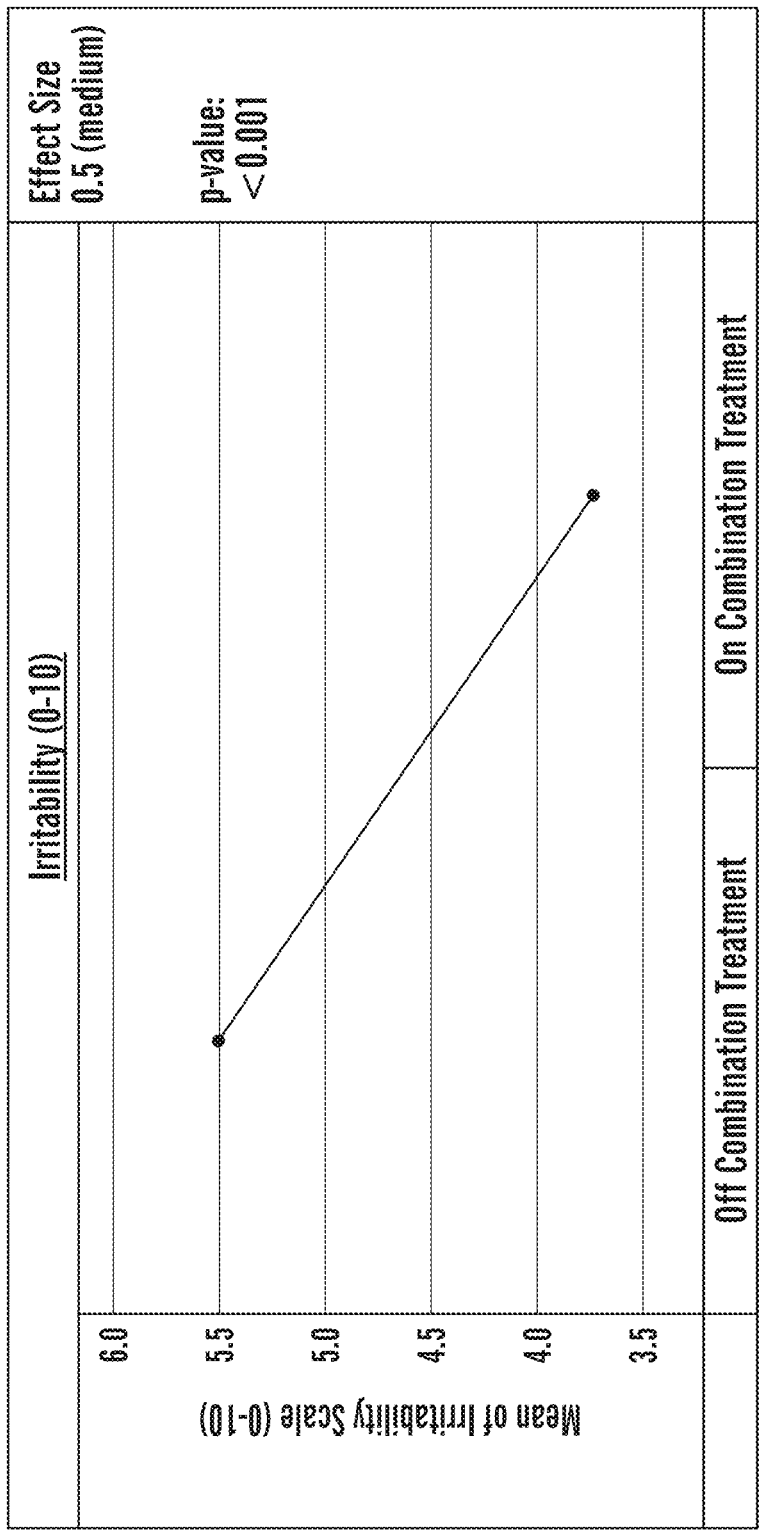
Figure 1E:
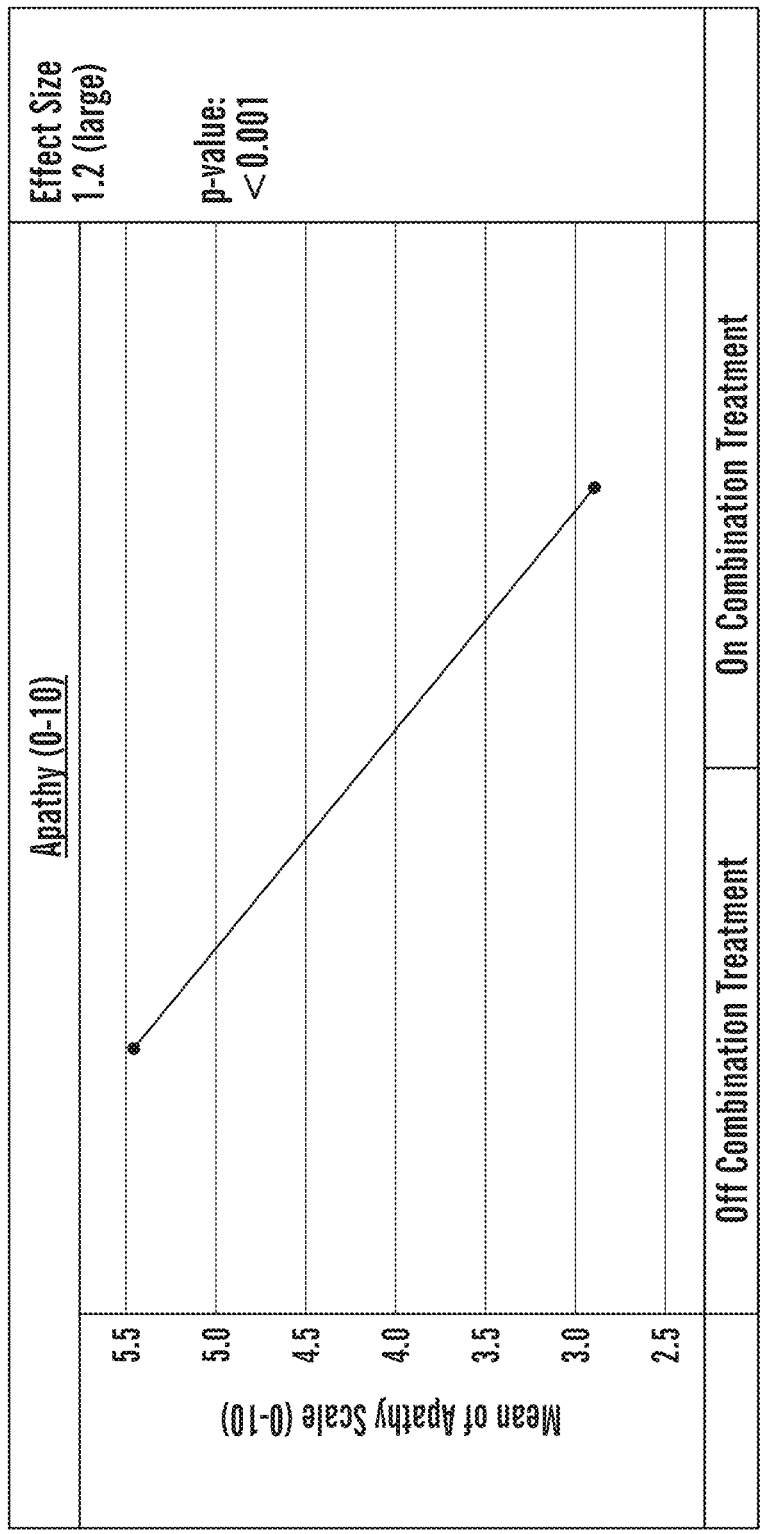
Figure 1F:
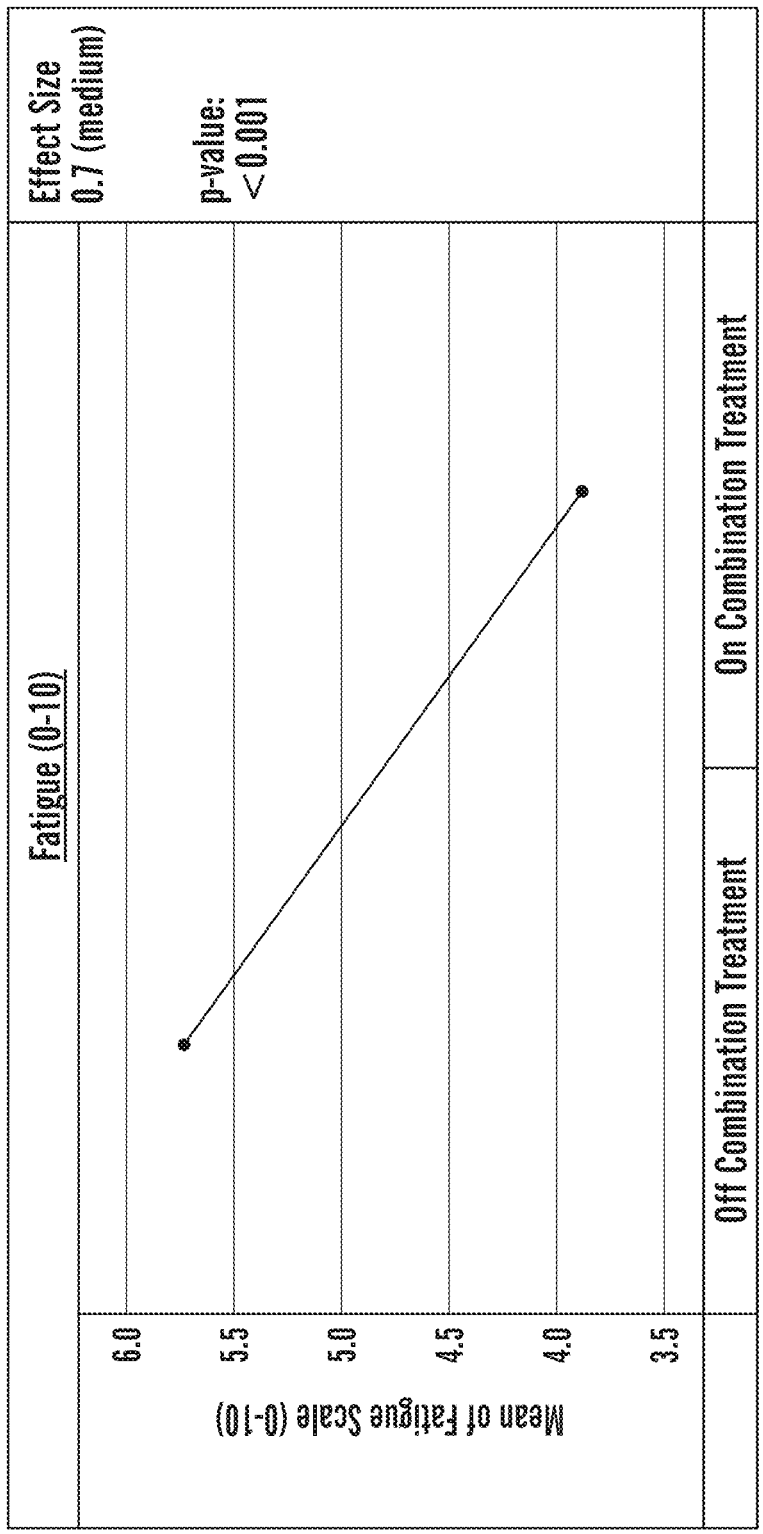
Figure 1G:
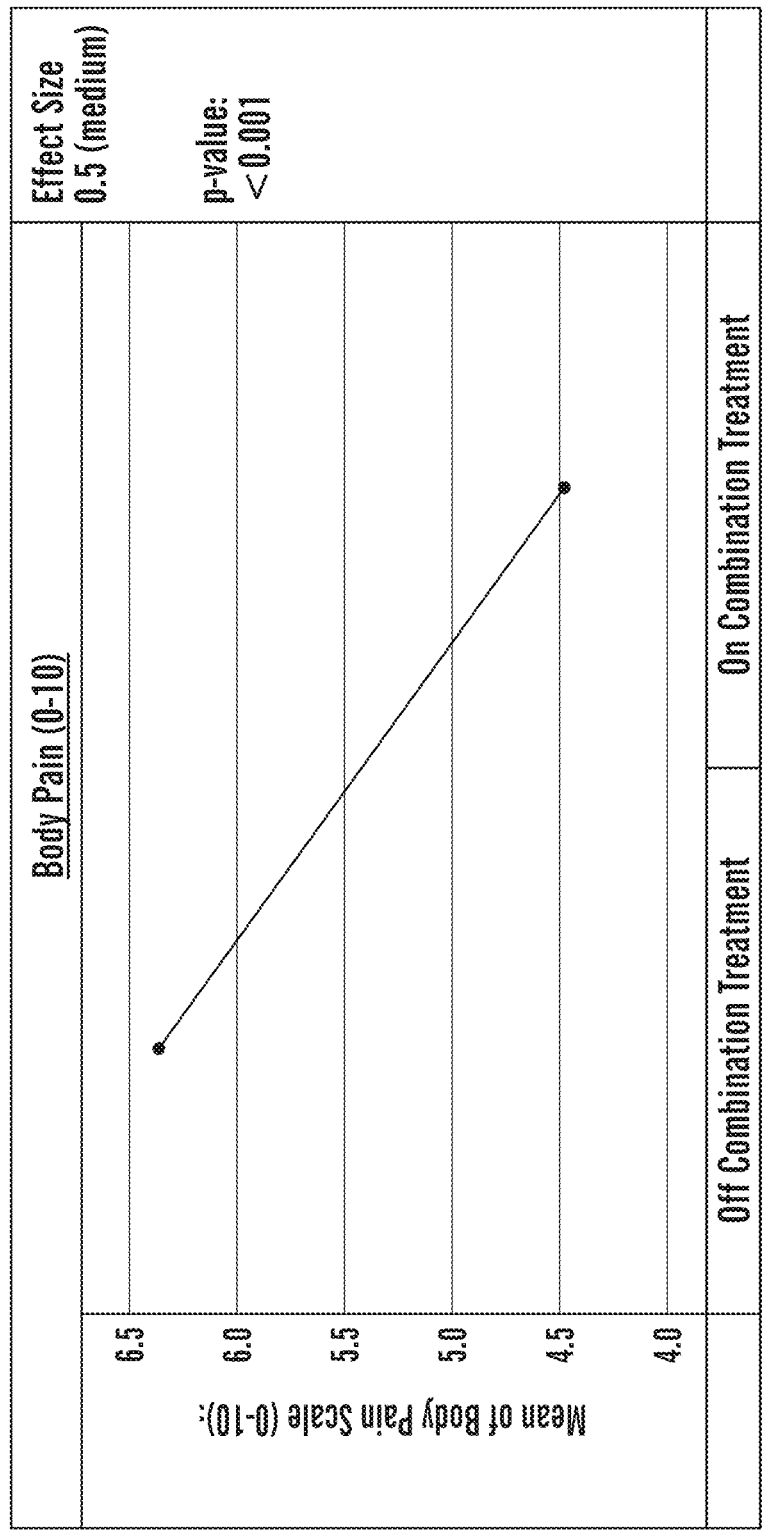
Figure 1H:
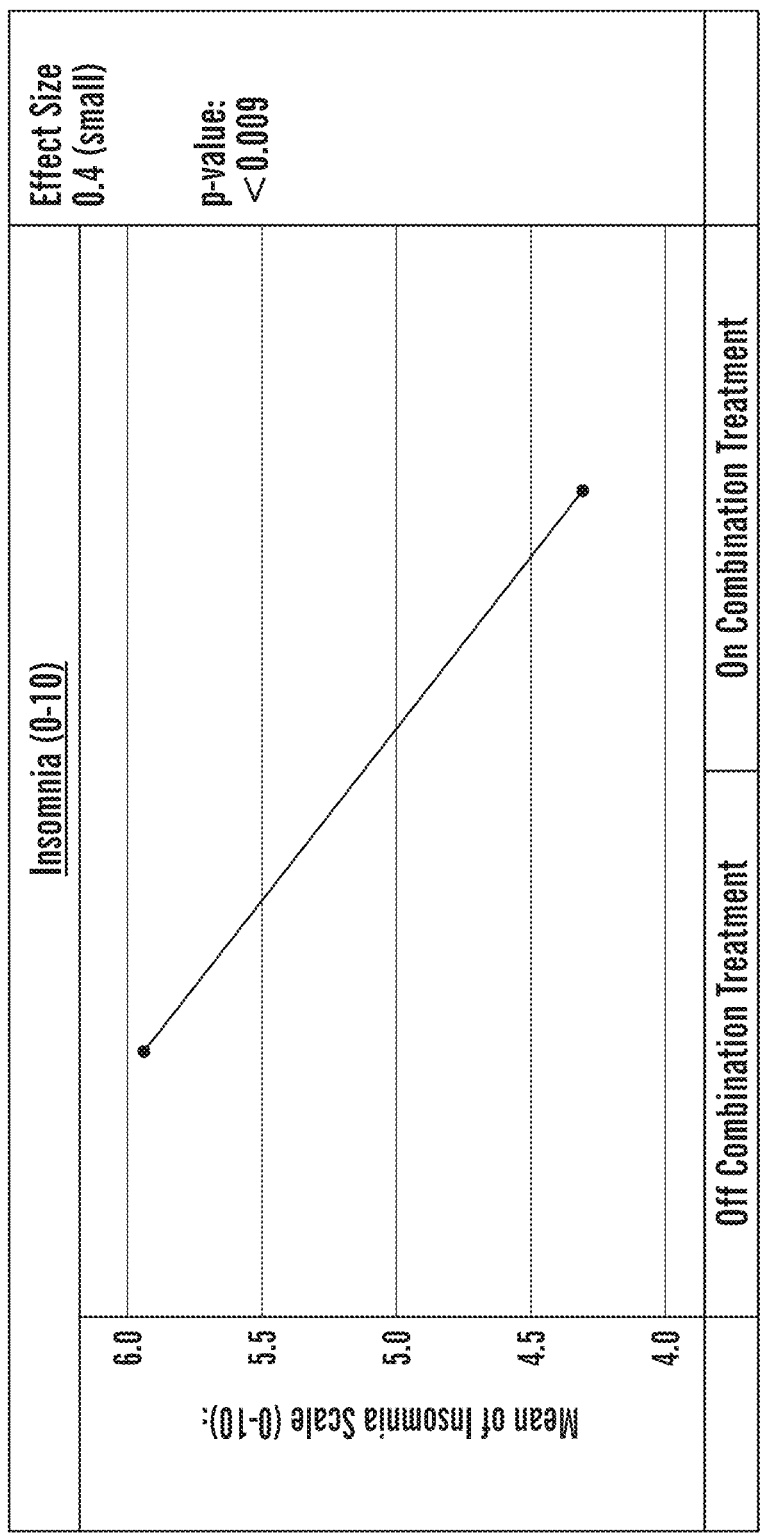
Figure 1I:
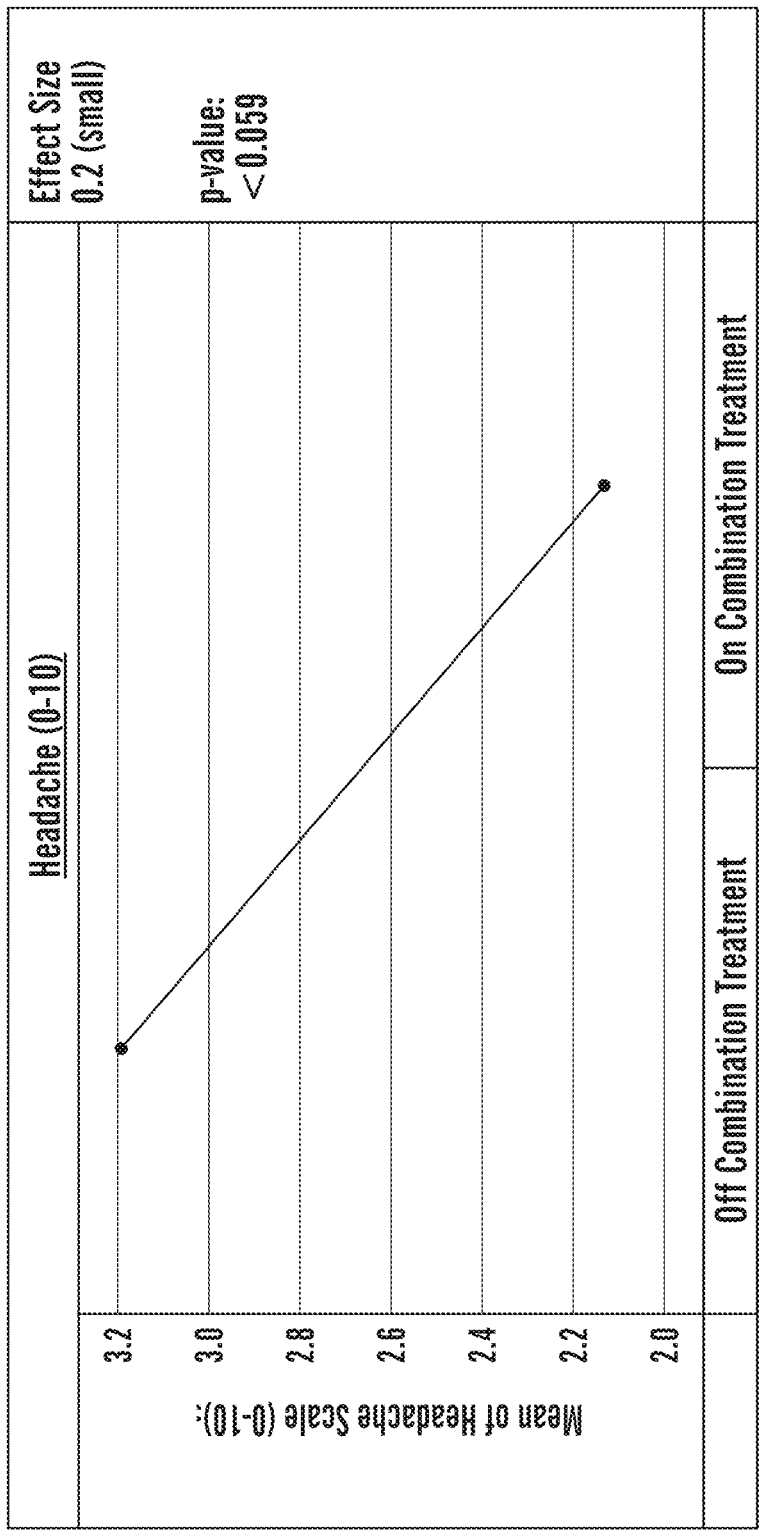
Figure 1J:
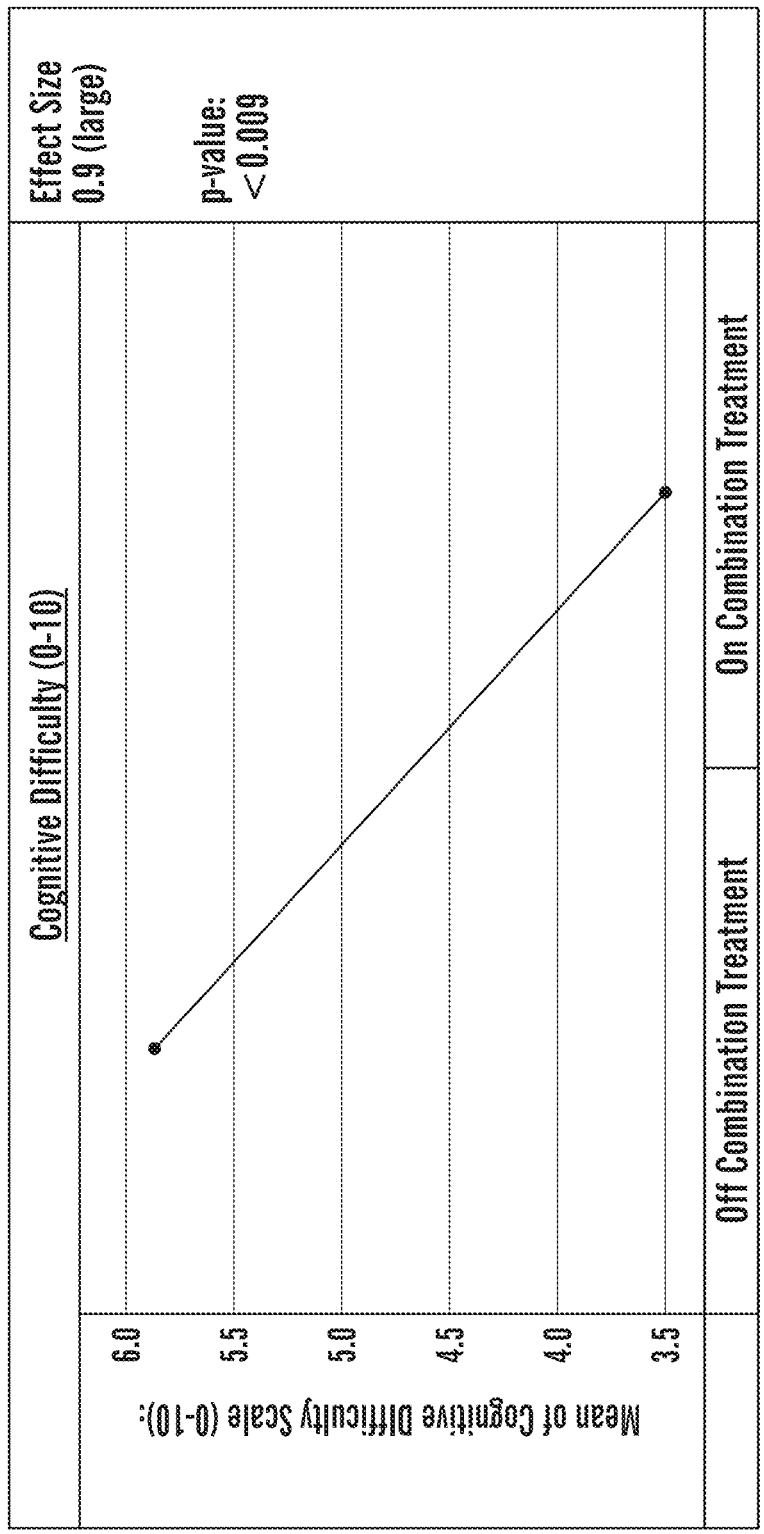
Figure 2A:
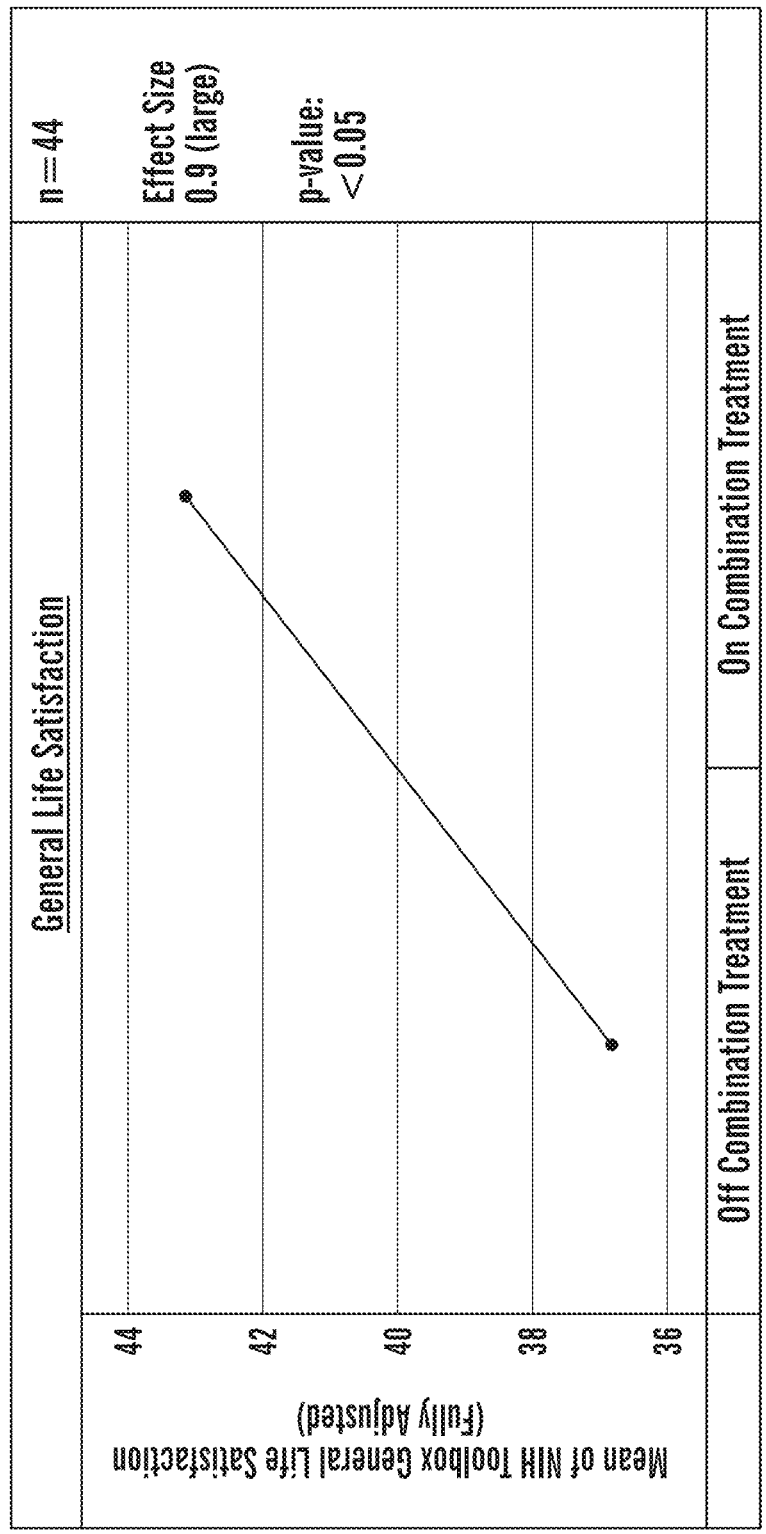
FIGS. 2A-2F illustrate differences in standardized psychosocial outcomes between patients on vs. off the combination therapy.
Figure 2B:
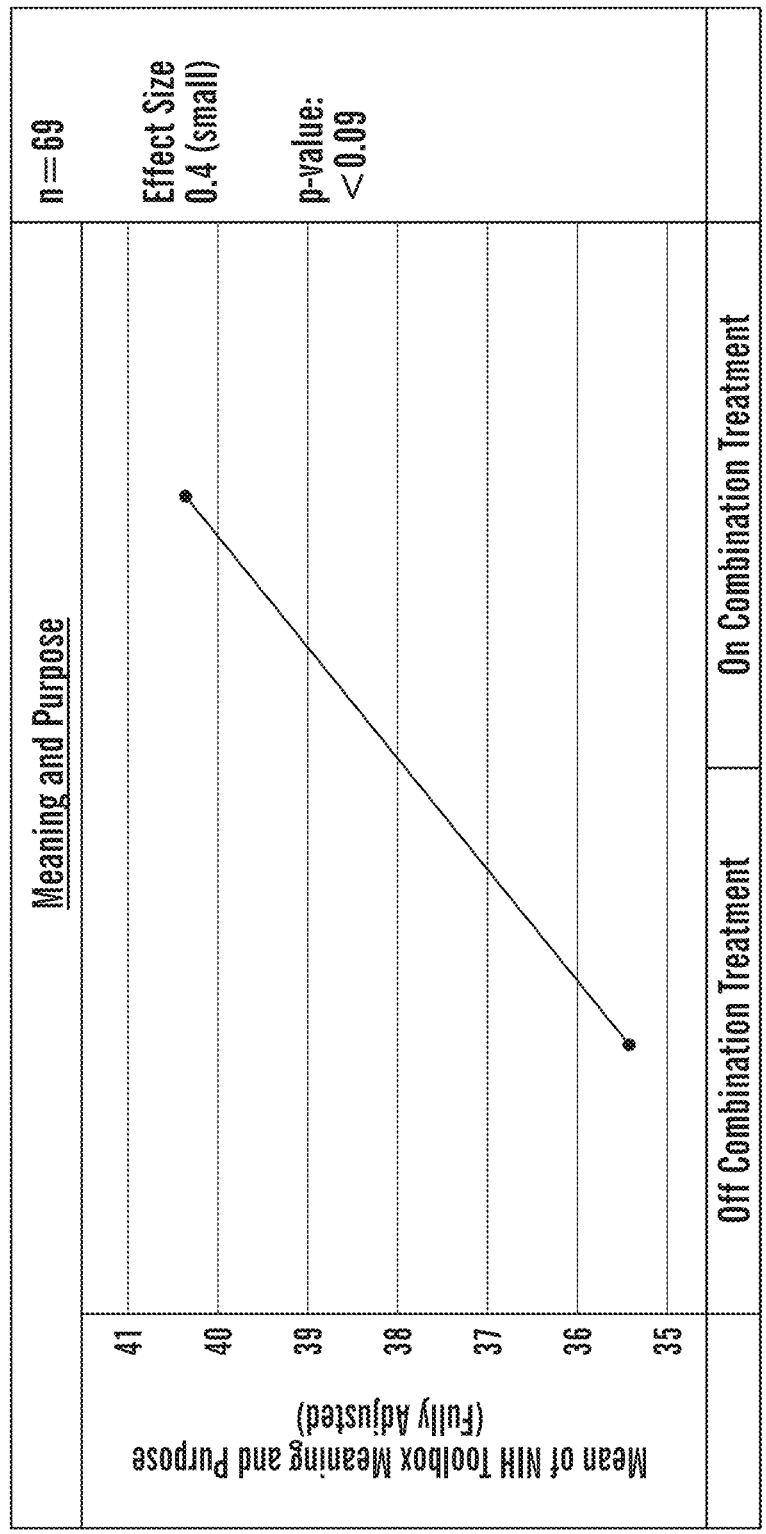
Figure 2C:
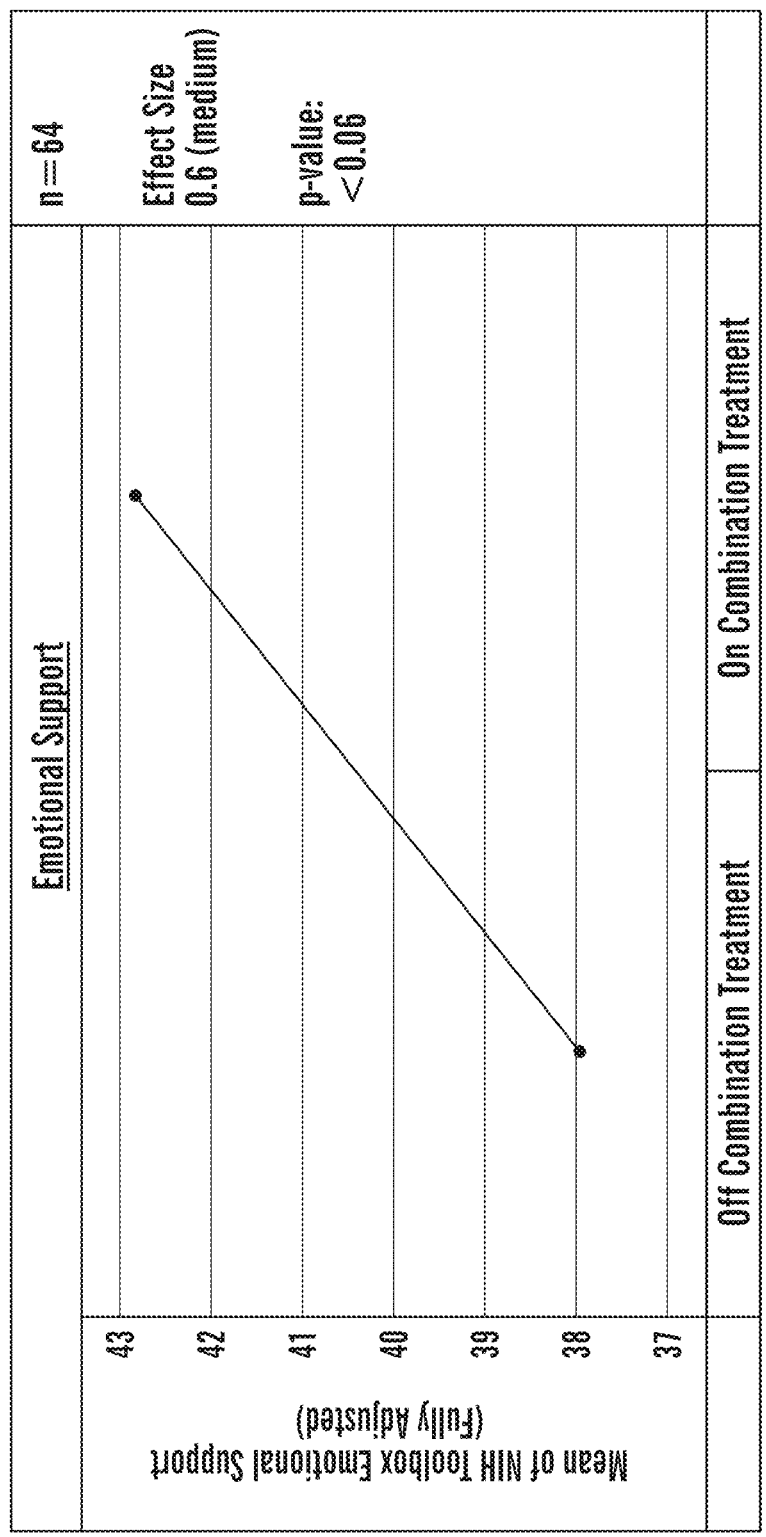
Figure 2D:
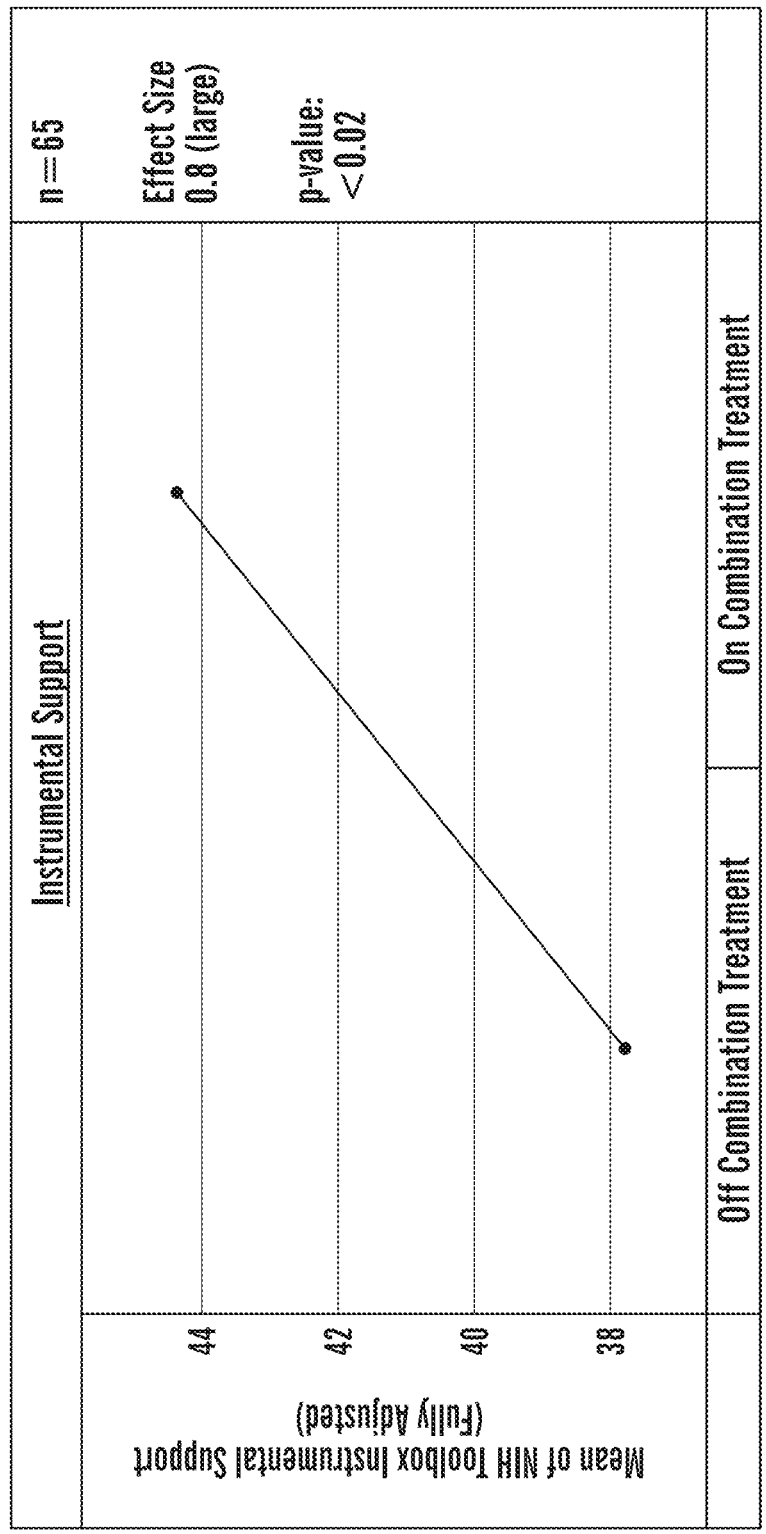
Figure 2E:
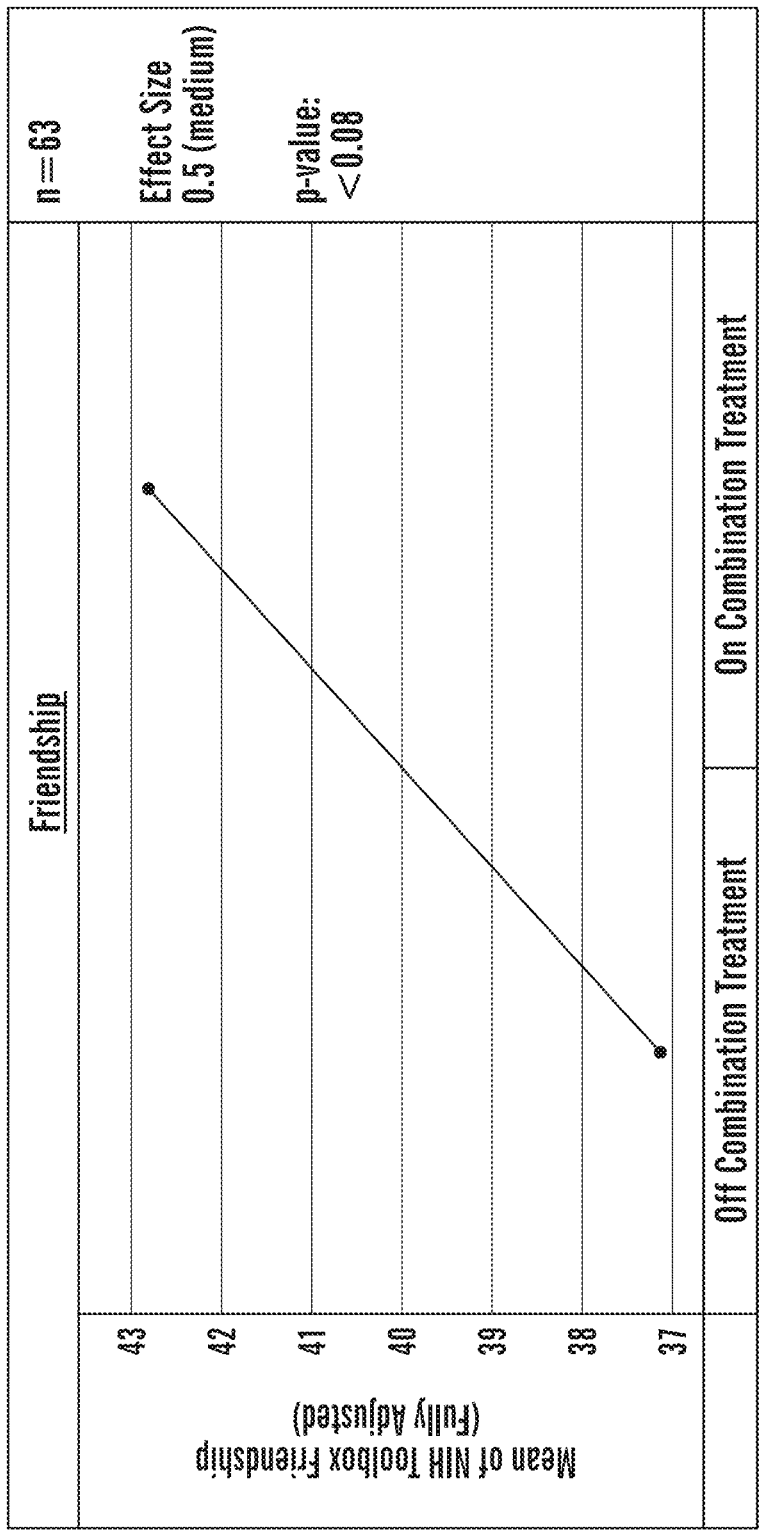
Figure 2F:
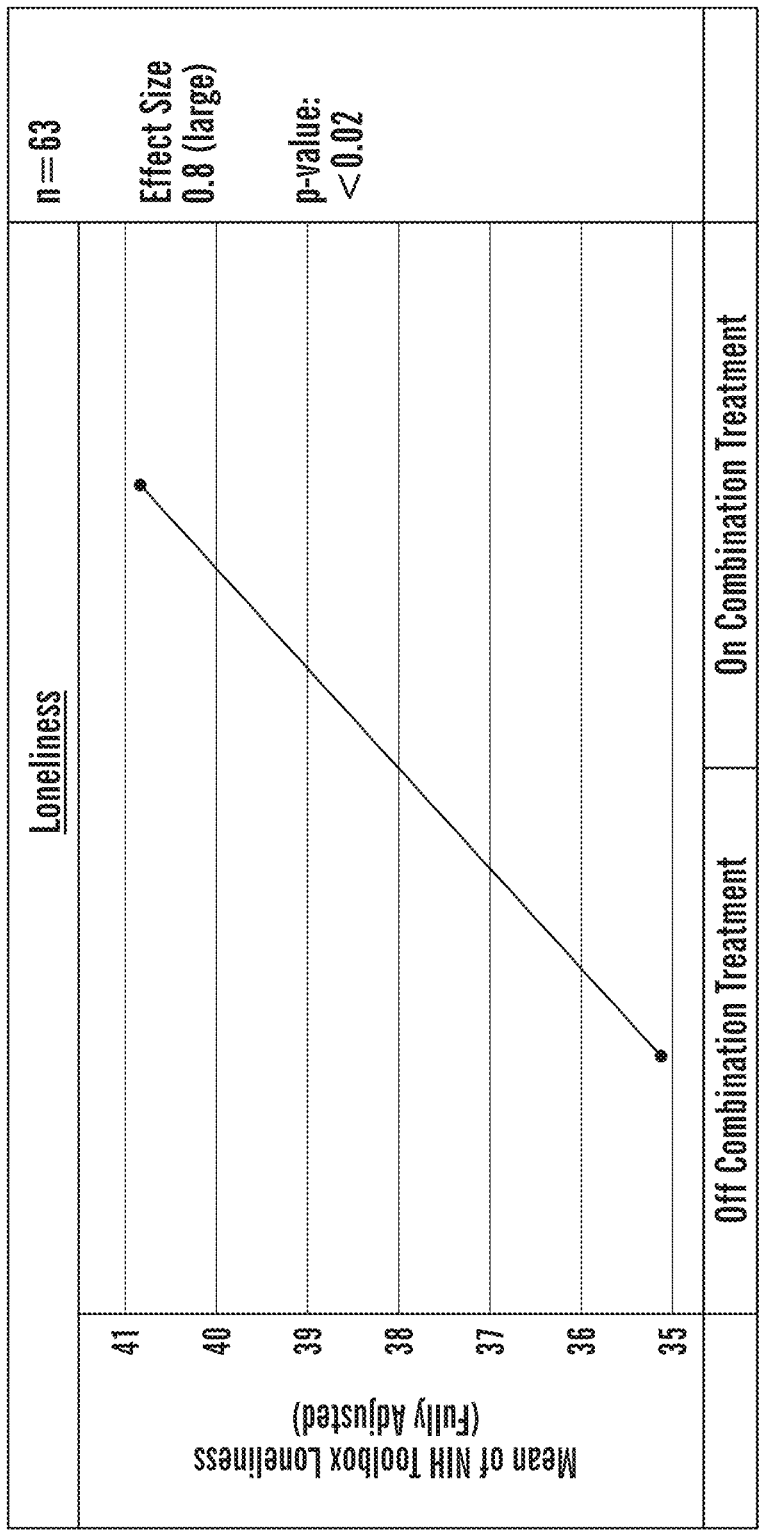

The invention features compositions and methods that are useful for the treatment of brain and/or behavioral health disorders, and their associated symptoms.

The invention is based, at least in part, on the discovery that a combination therapy comprising an agent that targets the adrenergic system (e.g., verapamil or other compounds with calcium channel blocking activity) and an agent that targets the renin angiotensin aldosterone system (RAAS) (e.g., telmisartan) effectively treated brain and/or behavioral health disorders and significantly reduced associated symptoms. In view of this surprising discovery, one of skill in the art would understand that any agent that targets the RAAS (e.g., telmisartan, candesartan) could be combined with any agent that targets the adrenergic system (e.g., anipamil, devapamil, falipamil, gallopamil, tiapamil, and verapamil) for the treatment of brain and/or behavioral health disorders and their associated symptoms. In particular, as reported in detail below, verapamil and telmisartan were effective at reducing or eliminating anxiety, apathy, cognitive difficulty, depression, fatigue, headache, insomnia, irritability, and chronic pain. Significantly, verapamil and telmisartan not only reduced such symptoms in treated subjects, but also produced a number of positive changes in such subjects, including an increase in general life satisfaction and meaning and purpose. Without intending to be bound by theory, it is likely that the combination of verapamil and telmisartan simultaneously targeted stress-induced hormones in both the body and the brain that collectively influence brain function.

Brain and Behavioral Disorders

Collectively, brain and behavioral disorders are the number one cause of disability worldwide. Achieving comprehensive remission, across the spectrum of so many different symptoms, is difficult for most patients, doctors and families because in real clinical practice, patients have multiple co-morbid diagnoses. Treating a patient with multiple co-morbidities requires separate individual treatment for each disorder, which increases complexity, inflates cost and lowers safety of care.

Brain and behavioral health disorders, at least partially due to having multiple components, result in serious psychosocial issues that negatively impact a patient's quality of life. However, current treatments are designed to treat only a single (e.g., neurological) component.

Although brain and behavioral health disorders are a clinically diverse group of disorders, abnormal functional connectivity represents a shared, common pathological framework. Regardless of the disorder, two independent systems, the adrenergic system and the brain renin angiotensin aldosterone system, directly influence functional connectivity. Across these disorders, abnormalities within one network tend to disrupt the function of related networks. For example, anxiety disorders and chronic pain can be classified, together, as reactive disorders, each featuring atypical connectivity between sensorimotor and salience networks. In fact, successful treatment of symptoms for many brain and behavioral disorders has been shown to be associated with normalization of atypical patterns of regional cerebral blood flow.

Non-limiting examples of brain and behavioral health disorders include affective disorders, anxiety disorders, neurodegenerative disorders, neurodevelopmental disorders, psychotic disorders, personality disorders, migraine disorders and somatosensory somatoform disorders. Examples of affective disorders include bipolar disorder, cyclothymia, depression, dysthemia, generalized anxiety disorder, major depressive disorder, obsessive compulsive disorder, postpartum depression, post-traumatic stress disorder (PTSD), phobias, and seasonal affective disorder. Examples of anxiety disorders include panic disorder, social anxiety disorder, post-traumatic stress disorder, obsessive compulsive disorder and specific phobia. Examples of neurodegenerative disorders include Alzheimer's disease and Parkinson's disease. Examples of neurodevelopmental disorders include autism spectrum disorder, attention deficit hyperactive disorder (ADHD) and learning disorders. Examples of psychotic disorders include schizophrenia, schizoaffective disorder and major depression with psychosis. Examples of personality disorders include paranoid, schizoid, schizotypal, antisocial, borderline, histrionic, narcissistic, avoidant, dependent and obsessive-compulsive personality disorder. Examples of somatosensory disorders include chronic pain and migraine-related disorders include migraine with aura, migraine without aura, acephalgic migraine, and basilar migraine. Examples of somatoform disorders include somatization disorder, hypochondriasis, conversion disorder, body dysmorphic disorder and chronic pain. The symptoms associated with the disease is selected from one or more of the "ten cardinal symptoms" associated with brain and behavioral health disorders, including but not limited to anxiety, apathy, cognitive difficulty, depression, fatigue, headache, insomnia, irritability, body pain and psychosis. Such symptoms are measured using any of a variety of methods available to a practitioner, non-limiting examples of which are presented in Brenes, "Anxiety, Depression, and Quality of Life in Primary Care Patients", *Prim Care Companion J Clin Psychiatry*, 9:437-443 (2007) and in Julian, "Measures of Anxiety", *Arthritis Care Res*, 63:1-11 (2011).

No current treatments for the above listed disorders are designed to address the functional connectivity abnormalities that are germane to the disorders. Selective serotonin reuptake inhibitors ("SSRI's") have limited effectiveness for anxiety. Even with cognitive behavioral therapy and medication, treatment success remains limited. Since SSRI's do not treat symptoms caused by common anxiety co-morbidities such as ADHD, disability due to co-morbidities remains untreated in the majority of patients seeking relief for anxiety. For patients with ADHD, stimulants are not effective for, and can often exacerbate, co-morbid mood disorders. These are critical treatment gaps because the symptoms caused by psychiatric co-morbidities are often the most disabling. Moreover, current controlled treatment options, specifically benzodiazepines, stimulants and opiates, are dangerous due to exacerbation of co-morbid mood disorders, addiction and lethal overdose.

Combination Therapies

Certain existing pharmaceuticals that influence the adrenergic system and the brain renin angiotensin aldosterone system and never previously used in combination can be combined to create novel, synergistic changes in cerebral blood flow that translate into desirable clinical outcomes. Combination treatments of the present invention involve, for example, administering to a subject a combination of two or more agents selected from previously FDA-approved cardiovascular medications. The invention features combinations containing verapamil and telmisartan, verapamil and candesartan, as well as candesartan and/or telmisartan in combination with one or more of anipamil, devapamil, falipamil, gallopamil, tiapamil, and verapamil.

Individually, agents are selected to target the renin angiotensin aldosterone system and the adrenergic system. Telmisartan and candesartan, individually or in combination, balance the severity of the angiotensin response because they block angiotensin 2 receptors. Not wishing to be bound by theory, anipamil, devapamil, falipamil, gallopamil, tiapamil, and verapamil, individually or in combination, balance the severity of the adrenalin response because they influence output of norepinephrine from the midbrain. Since both the adrenergic system and the brain RAAS interact to modulate functional connectivity, combining agents that target each system independently creates synergistic effects resulting in novel treatment effects.

A novel treatment is presented herein that ameliorates the psychiatric, psychological and neurological components of disorders that manifest as one or more of the ten cardinal neuro-psychiatric symptoms (i.e., anxiety, apathy, cognitive difficulty, depression, fatigue, headache, insomnia, irritability, pain (e.g., body pain), and psychosis), regardless of the underlying diagnosis. Without intending to be bound by theory, compositions and/or dosage forms of the present invention containing a therapeutic combination (e.g., verapamil and telmisartan, verapamil and candesartan, and candesartan and/or telmisartan in combination with one or more of anipamil, devapamil, falipamil, gallopamil, tiapamil, and verapamil) target stress-induced hormones in different regions of the brain simultaneously. The combinations of agents described herein, targeting both the adrenergic and the brain RAAS simultaneously with positive pluri-network effects, has never been contemplated or studied until now.

Administration to a subject of the compositions and dosage forms of the present invention containing a first agent selected from one or more of anipamil, devapamil, falipamil, gallopamil, tiapamil, and verapamil and a second agent selected from one or more of candesartan and telmisartan, delivered simultaneously or sequentially as a combination treatment, is useful for the treatment of brain and/or behavioral disorders and their associated symptoms (i.e., anxiety, apathy, cognitive difficulty, depression, fatigue, headache, insomnia, irritability, body pain, and psychosis. The combination treatments lead to positive psychosocial outcomes which, over time, correlate with significant improvements in overall measures of quality of life. For example, the compositions are associated with achieving patient advances along Maslow's hierarchy of needs, which is comprehensive outcome in healthcare that reflects not only symptomatology but also impact across a broad range of social determinants of health. In some embodiments, therapeutic combinations described herein positively affect the well-being of a subject undergoing treatment (e.g., increasing cognitive function, increasing life satisfaction, increasing meaning and purpose, increasing emotional support, increasing instrumental support, increasing friendship, increasing life satisfaction).

Pharmacological Effects

Without intending to be bound by theory, the pharmacological effects of compositions comprising a first agent selected from one or more of anipamil, devapamil, falipamil, gallopamil, tiapamil, and verapamil and a second agent selected from one or more of candesartan and telmisartan relate to the physiology of adrenalin and brain renin angiotensin aldosterone systems (RAAS). When a human senses danger, two independent body systems change the intrinsic, functional connectivity of the brain.

The adrenergic system, also known as the sympathetic/parasympathetic system, influences functional connectivity via signaling by the neurotransmitter known as norepinephrine (aka "adrenalin"). When norepinephrine is produced in the adrenal gland, it travels to the brain, where it binds to beta receptors. When beta receptors bind norepinephrine, changes occur such as pupillary dilation, reduction of pain sensation, and increased vigilance.

The brain renin angiotensin aldosterone system, also known as the brain RAAS system, influences functional connectivity via the neurotransmitter known as angiotensin. When the angiotensin precursor is produced in the kidneys, it travels through the lung and to the brain, where it binds to angiotensin receptors. When brain angiotensin receptors bind angiotensin, changes occur in the coupling between arterioles and astrocytes, a process known as neurovascular coupling, which causes focal changes in cerebral blood flow.

Not intending to be bound by any particular mode of action, when the adrenalin and brain RAAS systems are activated, the functional connectivity of the brain changes. This change in connectivity is an evolutionarily-preserved stress response system that helps the brain to adapt to metabolic demand. If maintained chronically, this can create an unequilibrated state of functional connectivity which can be detrimental. Several factors can promote chronic disequilibrium, including the built environment, social determinants of health and individual differences. These factors can be especially challenging for patients with a brain and/or behavioral health disorder. Not being bound by theory, compositions comprising a first agent selected from one or more of anipamil, devapamil, falipamil, gallopamil, tiapamil, and verapamil and a second agent selected from one or more of candesartan and telmisartan can re-equilibrate the changes in functional connectivity that are associated with a brain and/or behavioral health disorder.

Not wishing to be bound by theory, combination treatments involve administering to a subject compositions comprising a first agent selected from one or more of anipamil, devapamil, falipamil, gallopamil, tiapamil, and verapamil and a second agent selected from one or more of candesartan and telmisartan. Such combinations act on central functional networks that are common to more than one neuropsychiatric disorder. Without intending to be bound by theory, the unique combination of an angiotensin II receptor blockade with a concomitant adrenergic blockade leads to re-equilibration of distribution of cerebral blood flow particularly in the diencephalon, which is the region of the brain important for social and emotional awareness. In other words, by influencing functional networks related to cognition (telencephalon) simultaneously with influencing functional networks related to emotion (mesencephalon), functional networks related to social cognition (diencephalon) are equilibrated. This hypothesis is based on findings of conspicuous social changes in patients who took combination therapy. For example, bi-directional changes were observed in social and dressing behavior in patients taking combination treatment. Specifically, introverted patients displayed more extraversion while on combination treatment, whereas extraverted patients displayed more introversion while on combination treatment. The results of a study described in the Examples provided herein showed an improvement in social satisfaction in patients on combination treatment. The hypothesis that combination treatment leads to equilibrating effects in functional brain networks is further supported by analyses of results from the Weber test, performed as part of routine visits, which measures sensorineural function, which is influenced by lateralization of the brain's auditory functional network. In the clinic, patients who initiated combination treatment or changed from monotherapy to combination treatment displayed shifts from one visit to the next in lateralization of the Weber test. Shifts in lateralization of the Weber test do not occur with standard of care medications. Shifts in lateralization of the Weber do not occur when patients take the individual components of combination treatment. Remarkably, these shifts, like the changes in social outcomes, were bi-directional whereby some patients shifted towards the right and other patients shifted towards the left.

Not wishing to be bound by theory, the novel bi-directional outcomes associated with compositions comprising a first agent selected from one or more of anipamil, devapamil, falipamil, gallopamil, tiapamil, and verapamil and a second agent selected from one or more of candesartan and telmisartan suggest that combination treatment may serve a regulatory function in brain regions associated with the auditory and/or other functional brain networks. Since changes in auditory function correlated with clinical improvements in social function, therapeutic combinations described herein may affect not only auditory function, but also the interoceptive/exteroceptive awareness as well as the social communication skills that rely on auditory functioning. In fact, the auditory cortex participates directly in networks for emotional processing and communication (Disability and poor quality of life associated with comorbid anxiety disorders and physical conditions. Sareen J, Jacobi F, Cox B J, Belik S L, Clara I, Stein M B. Arch Intern Med. 2006 Oct. 23; 166(19):2109-16. doi: 10.1001/archinte.166.19.2109).

Compositions of the Invention Modulate Adrenergic and Angiotensin Function

Compositions comprising a first agent selected from one or more of anipamil, devapamil, falipamil, gallopamil, tiapamil, and verapamil and a second agent selected from one or more of candesartan and telmisartan comprise one ingredient for adrenergic modulation and one ingredient for brain RAAS. No pharmaceutical agents have been designed to target both systems simultaneously. This is a critical treatment gap because both of these systems interact when patients with brain and/or behavioral disorders experience the oft-untreatable symptoms that cause suffering.

The Adrenalin and Angiotensin Systems Affect Different Functional Brain Networks.

Without intending to be bound by theory, the effect of compositions comprising a first agent selected from one or more of anipamil, devapamil, falipamil, gallopamil, tiapamil, and verapamil and a second agent selected from one or more of candesartan and telmisartan depends in part on the relative density of the adrenalin and angiotensin receptors within each one of three phylogenetic levels of the brain. The mesencephalon is the oldest level of the brain, located at the bottom of the brain, just above the spinal cord. The telencephalon is the newest level of the brain to evolve, located at the top of the brain. Between these levels is the diencephalon. Not being bound by theory, each level of the brain contains brain regions rich with receptors that participate in several networks that subserve different neurological processes.

Since beta receptors (which bind norepinephrine) are located more densely within mesencephalon than telencephalon, the effect of norepinephrine is strongest in brain networks that rely on mesencephalic brain regions such as the brainstem. Since angiotensin receptors (which bind angiotensin) are located more densely within telencephalon than mesencephalon, the effect of angiotensin is strongest in brain networks that rely on telencephalic brain regions such as the prefrontal cortex. Clinically, modulating the adrenergic system influences neuropsychiatric symptoms (e.g., insomnia, fatigue, apathy, pain, anxiety) because mesencephalic networks have extensive connections to body organs. Modulating the angiotensin system influences different neuropsychiatric symptoms (e.g., cognitive impairment, headache, aura) because telencephalic networks have extensive connections to brain regions for sensory processing.

Figure 5:
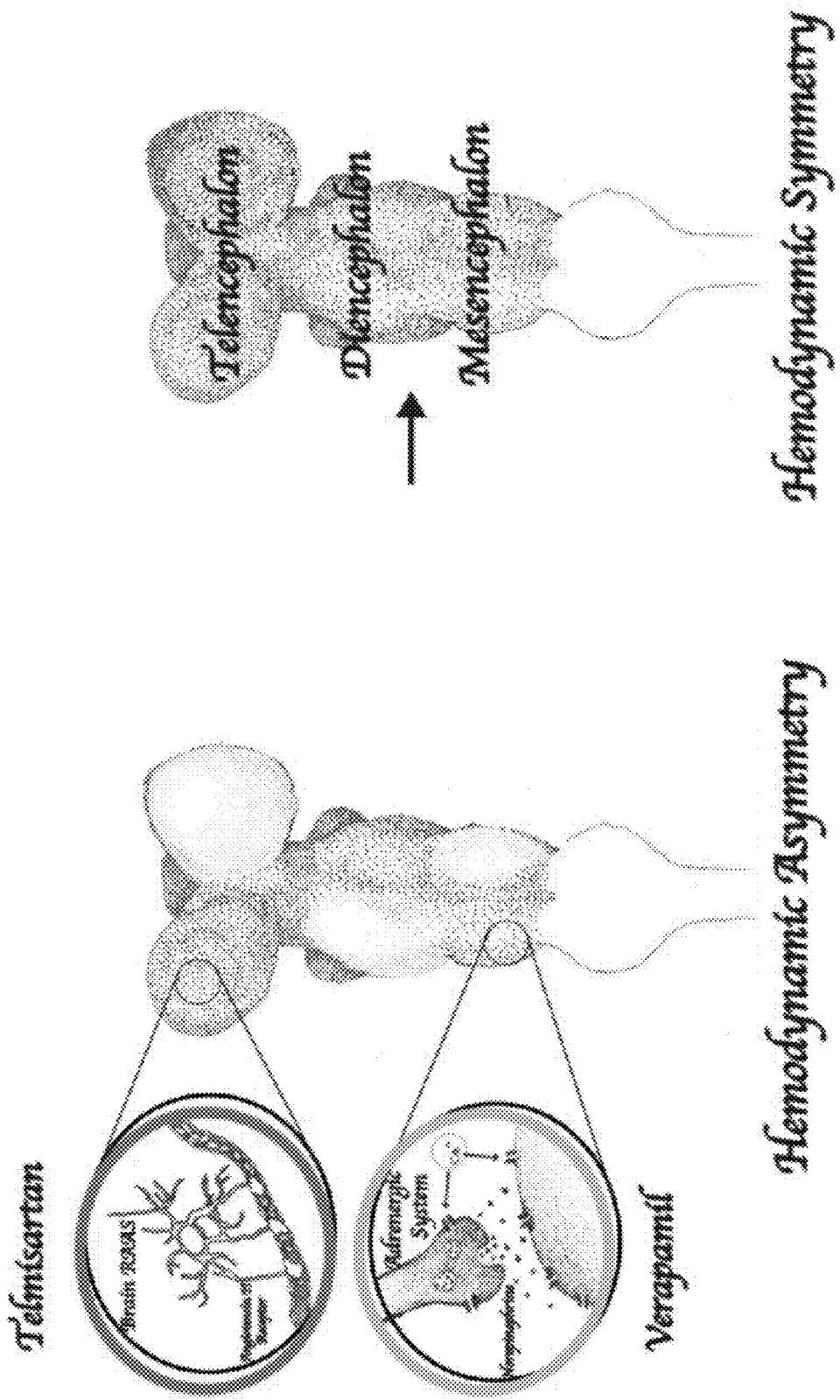
FIG. 5 is a diagram presenting a proposed mechanism of action of a composition containing verapamil and telmisartan. The figure depicts the brain in its embryological state before telencephalon, diencephalon and mesencephalon develop into cortex, subcortex and brainstem structures.

Each functional brain network spans different regions of the older and newer brain. The key functional brain networks implicated in brain and/or behavioral health disorders can include the default mode network, the salience, somatosensory, visual, auditory, and limbic networks, among others. Some of these brain networks rely heavily on newer brain regions. For example, the default mode network coordinates among regions mostly located within the telencephalon (the highest phylogenetic level). The salience network, on the other hand, coordinates regions within the mesencephalon (the lowest phylogenetically level).

systems (adrenalin system and brain RAAS). Each of these systems can play a key role in shifting functional connectivity of the brain as needed. Not being bound by theory, anipamil, devapamil, falipamil, gallopamil, tiapamil, verapamil, and combinations thereof interact with beta receptors within mesencephalon (FIG. 5). Not being bound by theory, telmisartan and candesartan interact with angiotensin receptors within telencephalon (FIG. 5).

Compositions comprising a first agent selected from one or more of anipamil, devapamil, falipamil, gallopamil, tiapamil, and verapamil and a second agent selected from one or more of candesartan and telmisartan, as detailed in the Examples below, have led to clinical effects that suggest a regulation in functional connectivity throughout the brain. The clinical effect of the compositions included normalization not only of emotional, but also social and cognitive symptoms due to the unique pluri-network effects achieved through this synergy. Not being bound by theory, since these

TABLE 1

Functional Brain Network Regions Organized by Phylogenetic Levels

| | Telencephalon | Diencephalon | Mesencephalon |
|---|---|---|---|
| Salience Network | Dorsal anterior cingulate/paracingulate cortex Frontoinsular cortices. Anterior insula Putamen Anterior temporal pole | Hypothalamus Dorsomedial thalamus | Sublenticular extended amygdala Ventral striatopallidum Periaqueductal gray Substantia nigra/ventral tegmental area |
| Default Mode Network | Posterior cingulate cortex Retrosplenial cortex VM prefrontal cortex AM prefrontal cortex Dorsal prefrontal cortex Temporal pole Middle temporal gyrus Hippocampus Parahippocampal cortex Amygdala Posterior parietal cortex Basal forebrain | Thalamus | Medial mesencephalic regions |
| Somatosensory | Primary somatosensory cortex Primary motor cortex Somatosensory association cortex | | |
| Visual | primary somatosensory cortex primary motor gyrus angular gyrus lateral occipital cortex mid-cingulate cortex anterior cingulate cortex supplementary motor area inferior frontal gyrus precentral gyrus temporal pole precuneous | | |
| Auditory Network | Bilateral superior temporal gyrus specifically Heschl's gyrus and Planum temporale | | |
| Limbic | Hippocampus | Hypothalamus Anterior Thalamic Nuclei | |

Therapeutic Combinations of the Invention Normalize Whole Brain Functional Connectivity.

Figure 6:
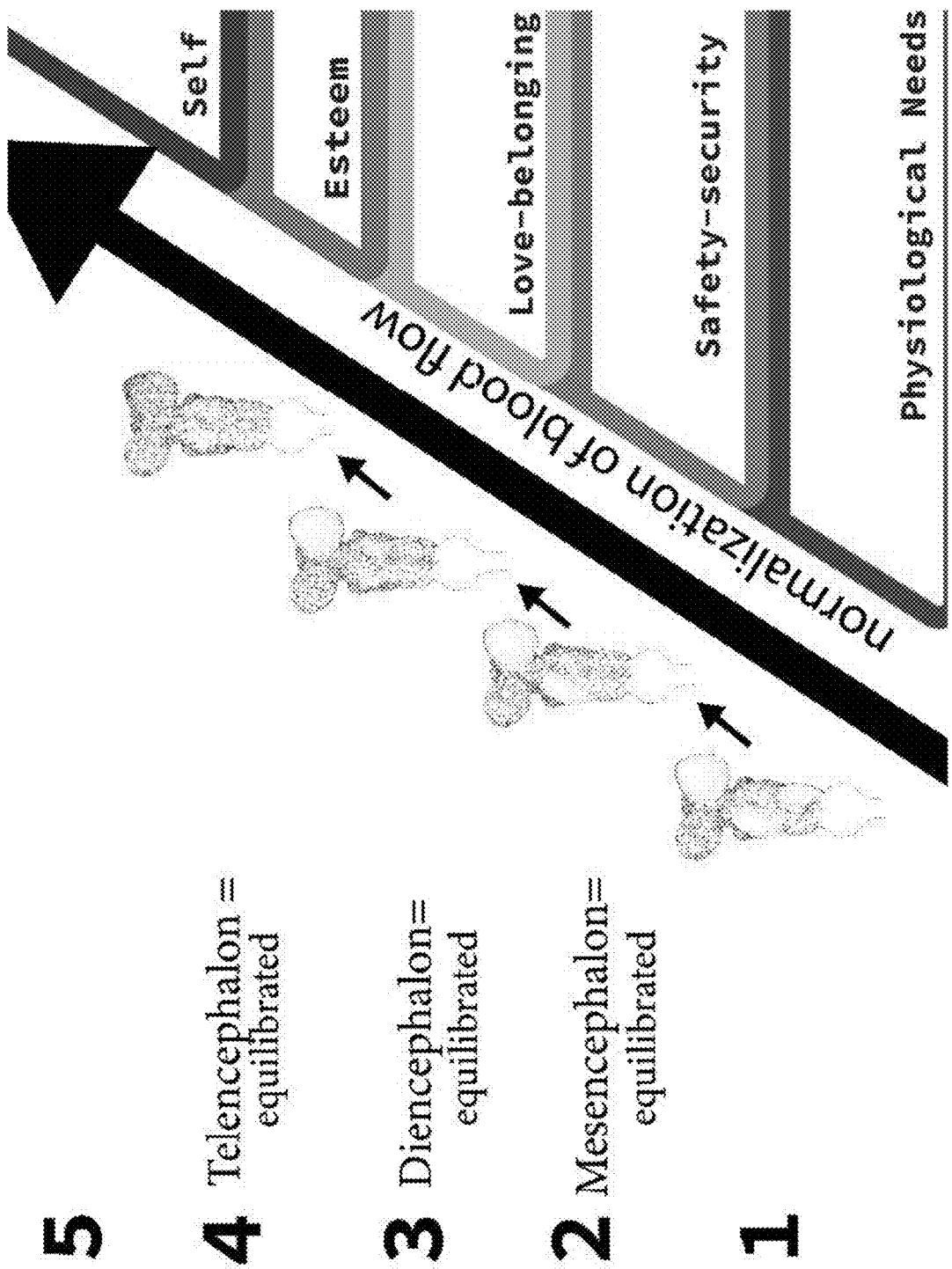
FIG. 6 is a schematic illustrating how a composition containing verapamil and telmisartan is hypothesized to enable progressive equilibration of cerebral blood flow as patients make psychosocial progress along Maslow's Hierarchy of Needs.

In embodiments, compositions comprising a first agent selected from one or more of anipamil, devapamil, falipamil, gallopamil, tiapamil, and verapamil and a second agent selected from one or more of candesartan and telmisartan achieve pluri-network effects because equilibration in lower brain networks influences equilibration of higher networks and vice versa. The compositions comprise at least two ingredients in order to block two different stress-related functions emanate from three distinct layers (diencephalon, mesencephalon and telencephalon), compositions comprising a first agent selected from one or more of anipamil, devapamil, falipamil, gallopamil, tiapamil, and verapamil and a second agent selected from one or more of candesartan and telmisartan alter connectivity at all three levels. The pluri-network effects of the compositions enable patients to make swift psychosocial progress (FIG. 6), which further improves whole brain connectivity (Safety Needs Mediate Stressful Events Induced Mental Disorders. Zheng Z, Gu S, Lei Y, Lu S, Wang W, Li Y, Wang F. Neural Plast. 2016; 2016:8058093. doi: 10.1155/2016/8058093. Epub 2016 Sep. 21). Not being bound by theory, improvement in symptomatology referable to all three phylogenetic levels does not occur when either agent is administered alone. Improvement in symptomatology referable to all three phylogenetic levels does not occur with any known standard of care treatment.
Prevention of Brain and/or Behavioral Health Disorders, and Medical Disorders The pluri-network effects of compositions comprising a first agent selected from one or more of anipamil, devapamil, falipamil, gallopamil, tiapamil, and verapamil and a second agent selected from one or more of candesartan and telmisartan discussed herein suggest that treatment with the compositions can treat disorders (e.g., panic disorder) affecting different parts of the brain at different times throughout the life course. Many neuropsychiatry disorders that are amenable to preventative treatment feature disequilibrium in more than one functional brain network, suggesting that these disorders are promising candidates for prophylactic treatment with a combination therapy described herein. For example, chronic pain disorders, which become more refractory to treatment across the life course if unaddressed, feature abnormalities in visual, salience and default mode networks that can be detectable prior to the onset of significant disability. Neurodevelopmental disorders such as ADHD, autism spectrum disorder and learning disorder, which become more refractory to treatment across the life course if unaddressed, feature pluri-network changes. Psychotic disorders such as schizophrenia, which becomes more refractory to treatment across the life course if unaddressed, feature functional abnormalities in multiple brain networks. Anxiety disorders become more refractory to treatment across the life course if unaddressed and show pluri-network effects, with some specific differences according to the disorder. Compositions comprising a first agent selected from one or more of anipamil, devapamil, falipamil, gallopamil, tiapamil, and verapamil and a second agent selected from one or more of candesartan and telmisartan are a promising preventative treatment for these conditions because they can improve whole brain functional connectivity despite individual differences in network dis-equilibration among the disorders. No current treatments are available to prevent neuropsychiatric disorders that worsen if left unmitigated across the life course. No research has ever been done regarding use of such compositions for prevention of neuropsychiatric disease or disability.

Compositions comprising a first agent selected from one or more of anipamil, devapamil, falipamil, gallopamil, tiapamil, and verapamil and a second agent selected from one or more of candesartan and telmisartan can be used for prevention of neurodegenerative disease risk beginning in midlife. The compositions can cumulatively normalize cerebral metabolism, which can be dysregulated in preclinical neurodegenerative disease states. Different Neurodegenerative disorders such as Alzheimer's disease, Parkinson's disease and frontotemporal lobar degeneration feature disequilibrium in different brain networks that stem from abnormal cerebral metabolism. No current treatments are available that can normalize cerebral metabolism in patients at risk for neurodegenerative diseases. Use of such compositions has never been studied in the context of neurodegenerative disease prevention or treatment.

Since compositions comprising a first agent selected from one or more of anipamil, devapamil, falipamil, gallopamil, tiapamil, and verapamil and a second agent selected from one or more of candesartan and telmisartan can normalize whole brain cerebral connectivity, the compositions can be used for certain indications that are outside the boundaries of neuropsychiatry (i.e., cancer, autoimmune, autonomic, among others). Dysregulated functional connectivity can affect risk for medical disorders because brain connectivity affects the health of the immune system. Specifically, medical disorders that conspicuously present around developmental windows (such as age 25, when the brain finishes myelinating) are candidates for a novel, brain-based, preventative treatment including treatment with the compositions.
Pharmaceutical Compositions The disclosure provides pharmaceutical compositions comprising an effective amount of a first agent selected from one or more of anipamil, devapamil, falipamil, gallopamil, tiapamil, and verapamil and an effective amount of a second agent selected from one or more of candesartan and telmisartan. Such combinations may be co-formulated or formulated separately but administered concurrently or sequentially. When the first and second agents are administered in combination, they are useful for the treatment of brain and/or behavioral health disorders (e.g., panic disorder). In some embodiments, the combination therapy is administered to treat one or more of the ten cardinal neuro-psychiatric symptoms (i.e., anxiety, apathy, cognitive difficulty, depression, fatigue, headache, insomnia, irritability, body pain, and psychosis).

In embodiments, the compositions of the present invention contain a first agent selected from one or more of anipamil, devapamil, falipamil, gallopamil, tiapamil, and verapamil and a second agent selected from one or more of candesartan and telmisartan for use in a combination treatment. In embodiments, the first agent is verapamil and the second agent is telmisartan and/or candesartan. In some cases, the first agent is selected to influence the beta receptors in the mesencephalon and the second agent is selected to interact with angiotensin receptors in the telencephalon. The agents can be selected so that the first agent influences the adrenalin system and the second agent influences the brain renin angiotensin aldosterone system. In embodiments, the compositions are associated with modulation of both adrenergic and angiotensin function.

In certain embodiments, the compositions of the present invention can prevent, inhibit, or disrupt, or reduce by at least 10%, 25%, 50%, 75%, or even 100% one or more of anxiety, migraine, depression, cognitive difficulty, anger, apathy, fatigue, body pain, psychosis, and insomnia that manifest in individuals afflicted with a disorder having one or more psychiatric, psychological and/or neurological components.

Pharmaceutically acceptable salts of anipamil, candesartan, devapamil, falipamil, gallopamil, telmisartan, tiapamil, and verapamil, or combinations thereof are contemplated herein for the treatment of one or more of the ten cardinal neuropsychiatric symptoms (i.e., anxiety, apathy, cognitive difficulty, depression, fatigue, headache, insomnia, irritability, body pain, and psychosis). The term "pharmaceutically acceptable salt" also refers to a salt prepared by contacting an agent (e.g., anipamil, candesartan, devapamil, falipamil, gallopamil, telmisartan, tiapamil, or verapamil), where the agent has an acidic functional group (e.g., a carboxylic acid functional group), with a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)-amine, 2-hydroxy-tert-butylamine, or tris-(hydroxymethyl)methylamine, N, N,-di-lower alkyl-N-(hydroxy lower alkyl)-amines, such as N,N-dimethyl-N-(2-hydroxyethyl)-amine, or tri-(2-hydroxyethyl)amine; N-methyl-D-glucamine; and amino acids such as arginine, lysine, and the like. The term "pharmaceutically acceptable salt" also refers to a salt prepared by contacting an agent (e.g., anipamil, candesartan, devapamil, falipamil, gallopamil, telmisartan, tiapamil, or verapamil), where the agent has a basic functional group (e.g., an amino functional group), with a pharmaceutically acceptable inorganic or organic acid. Suitable acids include, but are not limited to, hydrogen sulfate, citric acid, acetic acid, oxalic acid, hydrochloric acid, hydrogen bromide, hydrogen iodide, nitric acid, phosphoric acid, isonicotinic acid, lactic acid, salicylic acid, tartaric acid, ascorbic acid, succinic acid, maleic acid, besylic acid, fumaric acid, gluconic acid, glucaronic acid, saccharic acid, formic acid, benzoic acid, glutamic acid, methanesulfonic acid, ethanesulfonic acid, benzenesulfonic acid, and p-toluenesulfonic acid.

The compositions of the present invention can contain a salt of magnesium, optionally magnesium oxide (MgO).

Pharmaceutical Therapeutics

For therapeutic uses, compositions comprising a first agent selected from one or more of anipamil, devapamil, falipamil, gallopamil, tiapamil, and verapamil, and a second agent selected from one or more of candesartan and telmisartan can be administered systemically. Preferable routes of administration include, for example, oral administration or subcutaneous, intravenous, interperitoneally, intramuscular, or intradermal injections that provide continuous, sustained levels of the drug in the patient. Treatment of human patients or other animals will be carried out using a therapeutically effective amount (e.g., for treatment of a panic disorder) of a therapeutic identified herein in a physiologically-acceptable carrier. Anipamil, devapamil, falipamil, gallopamil, tiapamil, and/or verapamil in combination with candesartan and/or telmisartan can be formulated in a pharmaceutically-acceptable buffer such as physiological saline. Suitable carriers and their formulation are described, for example, in Remington's Pharmaceutical Sciences by E. W. Martin. The amount of the therapeutic agent to be administered varies depending upon the manner of administration, the age and body weight of the patient, and with the clinical symptoms of a brain and/or behavioral health disorder. The clinical symptoms, in some embodiments, are the ten cardinal neuropsychiatric symptoms (i.e., anxiety, apathy, cognitive difficulty, depression, fatigue, headache, insomnia, irritability, pain (e.g., body pain), and psychosis). Generally, amounts will be in the range of those used for other agents used in the treatment of a brain and/or behavioral health disorder. In some embodiments, a composition comprising verapamil and telmisartan, verapamil and candesartan, or candesartan and/or telmisartan in combination with one or more of anipamil, devapamil, falipamil, gallopamil, tiapamil, and verapamil is administered at a dosage that is effective at reducing one or more of the ten cardinal neuropsychiatric symptoms (i.e., anxiety, apathy, cognitive difficulty, depression, fatigue, headache, insomnia, irritability, body pain, and psychosis). Effectiveness of the administration can be determined by a method known to one skilled in the art, or using any assay that measures one or more of the ten neuropsychiatric symptoms (e.g., behavioral assessment, neuropsychological testing, etc.). For example, in some presently disclosed embodiments, effectiveness of the treatment can be measured by patient self-reports of symptoms and/or via NIH toolbox testing. Effectiveness can also be measured outcomes on disease-specific, gold-standard outcome measures, including measures that assess not only symptoms and function but also overall life satisfaction or quality of life.

Formulation of Pharmaceutical Compositions

The administration of a composition containing a first agent selected from one or more of anipamil, devapamil, falipamil, gallopamil, tiapamil, and verapamil and a second agent selected from one or more of candesartan and telmisartan can be administered to a subject for the treatment of a brain and/or behavioral health disorder (e.g., panic disorder) by any suitable means that results in a concentration of the therapeutic that, combined with other components, is effective in ameliorating, reducing, or stabilizing one or more of the ten cardinal neuropsychiatric symptoms. In some embodiments, the combination treats one or more of the ten cardinal neuropsychiatric symptoms (i.e., anxiety, apathy, cognitive difficulty, depression, fatigue, headache, insomnia, irritability, body pain, and psychosis). The compositions can contain a salt of magnesium, optionally magnesium oxide (MgO). The composition can be contained in any appropriate amount any suitable carrier substance, that is generally present in an amount of 1-95% by weight of the total weight of the composition. The composition can be provided in a dosage form that is suitable for oral administration. In some embodiments, the composition can be provided in a dosage form that is suitable for a parenteral (e.g., subcutaneously, intravenously, intramuscularly, or intraperitoneally) administration route. The pharmaceutical compositions can be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Human dosage amounts can initially be determined by extrapolating from the amount of anipamil, candesartan, devapamil, falipamil, gallopamil, telmisartan, tiapamil, verapamil, or combinations thereof, used in mice. Dosages can also be determined based on dosages for the effective treatment of disorders for which the individual agents have been indicated in humans. The dosage (optionally a daily dosage) amount of one or more of anipamil, devapamil, falipamil, gallopamil, tiapamil, and verapamil, individually or collectively, can be from about 120 mg to about 480 mg, from about 250 mg to about 360 mg, from about 200 mg to about 500 mg, from about 250 mg to about 350 mg, from about 120 mg to about 720 mg, or about 288 mg. The dosage amount of the second agent can be from about 80 mg to about 400 mg, from about 45 mg to about 180 mg, from about 80 mg to about 320 mg, from about 45 mg to about 150 mg, from about 90 mg to about 200 mg, or about 96 mg. In embodiments, the dosage amount of the second agent is greater than 70 mg, 75 mg, 80 mg, 85 mg, 90 mg, 95 mg, 100 mg, or 150 mg. The dosage of the first agent or components thereof and the second agent or components thereof can be contained in one or multiple dosage forms.

In some embodiments, the daily dosage of either the first or the second agent is administered more than once per day. For example, in some embodiments, the daily administration (e.g., 80 mg) is delivered in two 40 mg doses twice per day.

The first agent and the second agent can be administered to a subject (optionally as a dosage form) at a dosage ratio (mass:mass) of the first agent (e.g., anipamil, devapamil, falipamil, gallopamil, tiapamil, verapamil, or combinations thereof) to the second agent (e.g., candesartan, telmisartan, or combinations thereof) of about or at least about 1:1, 2:1, 3:1, 4:1, 5:1, 6:1, 7:1, or 8:1. In some embodiments, the dosage ratio of the first agent (e.g., anipamil, devapamil, falipamil, gallopamil, tiapamil, verapamil, or combinations thereof) to the second agent (e.g., candesartan, telmisartan, or combinations thereof) is less than about 3:1, 4:1, 5:1, 6:1, 7:1, or 8:1. The first agent (e.g., anipamil, devapamil, falipamil, gallopamil, tiapamil, verapamil, or combinations thereof) can be administered to a subject at a daily dosage that is about double or triple a daily dosage of the second agent (e.g., candesartan, telmisartan, or combinations thereof) administered to the subject. In some embodiments, the dosage amounts for the first agent (e.g., anipamil, devapamil, falipamil, gallopamil, tiapamil, verapamil, or combinations thereof), the second agent (e.g., candesartan, telmisartan, or combinations thereof), or components thereof (e.g., anipamil, candesartan, devapamil, falipamil, gallopamil, telmisartan, tiapamil, verapamil, or combinations thereof), individually or in combination, can vary from between about 0.1 mg compound/Kg body weight to about 2 mg compound/Kg body weight; or from about 0.5 mg/Kg body weight to about 2 mg/Kg body weight or from about 1.0 mg/Kg body weight to about 2 mg/Kg body weight; or from about 1.5 mg/Kg body weight to about 2 mg/Kg body weight; or from about 0.1 mg/Kg body weight to about 1.5 mg/Kg body weight; or from about 0.10 mg/Kg body weight to about 1.0 mg/Kg body weight; or from about 0.10 mg/Kg body weight to about 0.5 mg/Kg body weight. In other embodiments this dose can be about 0.1, 0.25, 0.5, 0.75, 1.0, 1.25, 1.5, 1.75, 2.0, 2.25, 2.5, 2. 75, or 3.0 mg/Kg body weight. In other embodiments, it is envisaged that doses can be in the range of about 0.2 mg compound/Kg body to about 2 mg compound/Kg body. Of course, the dosage amounts can be adjusted upward or downward, as is routinely done in such treatment protocols, depending on the results of the initial clinical trials and the needs of a particular patient.

The dosage amount (optionally a daily dosage) of a magnesium salt (e.g., MgO) in embodiments is about or at least about 100 mg, 150 mg, 200 mg, 250 mg, 300 mg, 350 mg, 400 mg, or 500 mg. The dosage amount (optionally a daily dosage) of a magnesium salt (e.g., MgO) in embodiments is no more than about 250 mg, 300 mg, 350 mg, 400 mg, 450 mg, or 500 mg.

Pharmaceutical compositions according to the presently disclosed embodiments can be formulated to release the active compound (e.g., anipamil, candesartan, devapamil, falipamil, gallopamil, telmisartan, tiapamil, and verapamil, or combinations thereof) substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (sawtooth kinetic pattern); (iv) formulations that localize action by, e.g., spatial placement of a controlled release composition near intended targeted cells (e.g., brain cells); (v) formulations that allow for convenient dosing, such that doses are administered, for example, orally once or twice per day; and (vi) formulations that target calcium channels and angiotensin receptors by using carriers or chemical derivatives to deliver the therapeutic agent to a particular cell type (e.g., brain cell). For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition can be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra.

Compositions for parenteral use can be provided in unit dosage forms (e.g., in single-dose ampoules), or in vials containing several doses and in which a suitable preservative can be added (see below). The composition can be in the form of a solution, a suspension, an emulsion, an infusion device, or a delivery device for implantation, or it can be presented as a dry powder to be reconstituted with water or another suitable vehicle before use. Apart from the active agent that reduces or ameliorates one or more of the ten cardinal neuropsychiatric symptoms (i.e., anxiety, apathy, cognitive difficulty, depression, fatigue, headache, insomnia, irritability, body pain, and psychosis), the composition can include suitable parenterally acceptable carriers and/or excipients. The active therapeutic agent(s) can be incorporated into microspheres, microcapsules, nanoparticles, liposomes, or the like for controlled release. Furthermore, the composition can include suspending, solubilizing, stabilizing, pH-adjusting agents, tonicity adjusting agents, and/or dispersing, agents.

As indicated above, the pharmaceutical compositions according to the presently disclosed embodiments can be in the form suitable for sterile injection. To prepare such a composition, one or more of anipamil, candesartan, devapamil, falipamil, gallopamil, telmisartan, tiapamil, and verapamil is dissolved or suspended in a parenterally acceptable liquid vehicle. Among acceptable vehicles and solvents that can be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation can also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent can include 10-60% w/w of propylene glycol or the like.

Controlled Release Parenteral Compositions

Controlled release parenteral compositions can be in form of aqueous suspensions, microspheres, microcapsules, magnetic microspheres, oil solutions, oil suspensions, or emulsions. Alternatively, the active drugs can be incorporated in biocompatible carriers, liposomes, nanoparticles, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that can be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Solid Dosage Forms for Oral Use

Formulations for oral use include tablets containing the active ingredients (e.g., one or more of anipamil, candesartan, devapamil, falipamil, gallopamil, telmisartan, tiapamil, and verapamil) in a mixture with non-toxic pharmaceutically acceptable excipients. Such formulations are known to the skilled artisan. Excipients can be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets are uncoated in some embodiments and coated in other embodiments. The tablets can be coated by known techniques, optionally to delay disintegration and absorption in the gastrointestinal tract and thereby provide a sustained action over a longer period. The coating can be adapted to release the active drug or drugs in a predetermined pattern (e.g., in order to achieve a controlled release formulation) or adapted not to release the active drug until after passage of the stomach (enteric coating). The coating, in some embodiments, is a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material, such as, e.g., glyceryl monostearate or glyceryl distearate can be employed.

The solid tablet compositions include, in some embodiments, a coating adapted to protect the composition from unwanted chemical changes, (e.g., chemical degradation prior to the release of the first and/or second agent). In some embodiments, the coating is applied on the solid dosage form in a similar manner as that described in Encyclopedia of Pharmaceutical Technology, supra.

One or more of anipamil, candesartan, devapamil, falipamil, gallopamil, telmisartan, tiapamil, and verapamil are mixed together in the tablet or partitioned. In one example, a first agent (e.g. one or more of anipamil, devapamil, falipamil, gallopamil, tiapamil, and verapamil) is contained on the inside of the tablet, and a second agent (e.g., one or more of candesartan and telmisartan) is on the outside, such that a substantial portion of the second agent is released prior to the release of the first agent. In some embodiments, the second agent (e.g., one or more of candesartan and telmisartan) is contained on the inside of the tablet and the first agent (e.g. one or more of anipamil, devapamil, falipamil, gallopamil, tiapamil, and verapamil) is on the outside.

Formulations for oral use include chewable tablets or hard gelatin capsules, wherein the active ingredients (i.e., anipamil, candesartan, devapamil, falipamil, gallopamil, telmisartan, tiapamil, and verapamil, or combinations thereof) are mixed with an inert solid diluent (e.g., potato starch, lactose, microcrystalline cellulose, calcium carbonate, calcium phosphate, or kaolin), or as soft gelatin capsules, wherein the active ingredients are mixed with water or an oil medium, for example, peanut oil, liquid paraffin, or olive oil. Powders and granulates are prepared in some embodiments using the ingredients mentioned above under tablets and capsules in a conventional manner using, e.g., a mixer, a fluid bed apparatus, or a spray drying equipment.

Controlled Release Oral Dosage Forms

Controlled release compositions of a first agent selected from one or more of anipamil, devapamil, falipamil, gallopamil, tiapamil, and verapamil and a second agent that is selected from one or more of candesartan and telmisartan (e.g., for oral use) can be constructed to release the agents by controlling the dissolution and/or the diffusion of the active substance. For example, an immediate release formulation is commercially available for verapamil and telmisartan, as are extended release versions of verapamil. The verapamil extended release (ER) formulations release the drug over 12 or 24 hours. Dissolution or diffusion-controlled release can be achieved by appropriate coating of a tablet, capsule, pellet, or granulate formulation of compounds, or by incorporating a composition comprising the first and/or second agents into an appropriate matrix or matrices. A controlled release coating includes, in some embodiments, one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material can also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing two agents described herein (e.g., one or more of verapamil, anipamil, devapamil, falipamil, gallopamil, and tiapamil and one or more of telmisartan and candesartan) is, in some embodiments, in the form of a buoyant tablet or capsule (i.e., a tablet or capsule that, upon oral administration, floats on top of the gastric content for a certain period of time). A buoyant tablet formulation of the composition can be prepared by granulating a mixture of one or more of the agents, or components thereof, with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

The presently disclosed embodiments provide methods of treating one or more of the ten cardinal neuropsychiatric symptoms (i.e., anxiety, apathy, cognitive difficulty, depression, fatigue, headache, insomnia, irritability, body pain, and psychosis) that comprise administering a therapeutically effective amount of a pharmaceutical composition(s) comprising the first agent (e.g., one or more of anipamil, devapamil, falipamil, gallopamil, tiapamil, and verapamil) and the second agent (e.g., one or more of candesartan and telmisartan) to a subject (e.g., a mammal such as a human). Thus, one embodiment is a method of treating a subject suffering from or susceptible to a disease or disorder that causes one or more of the ten cardinal neuropsychiatric symptoms (i.e., anxiety, apathy, cognitive difficulty, depression, fatigue, headache, insomnia, irritability, body pain, and psychosis). The method includes the step of administering to the subject a therapeutic amount of a combination of the first agent and the second agent sufficient to treat the disease, condition, disorder or symptom thereof, under conditions such that the disease, condition, disorder or symptom thereof is treated. The therapeutic methods include prophylactic treatment. In some embodiments, the subject is a mammal, particularly a human suffering from, having, susceptible to, or at risk for disease or disorder that causes one or more of the ten cardinal neuropsychiatric symptoms (i.e., anxiety, apathy, cognitive difficulty, depression, fatigue, headache, insomnia, irritability, body pain, and psychosis).

Identifying a subject in need of such treatment can be in the judgment of a subject or a health care professional and can be subjective (e.g. opinion) or objective (e.g. measurable by a test or diagnostic method).

Combination Therapies

Optionally, the first agent (e.g., one or more of anipamil, devapamil, falipamil, gallopamil, tiapamil, and verapamil) and/or the second agent (e.g., one or more of candesartan and telmisartan), can be administered together with any other standard anti-anxiety, anti-migraine, anti-depression, anti-cognitive difficulty, anti-anger, anti-apathy, anti-fatigue, anti-pain, anti-psychosis, or anti-insomnia therapy such as cognitive behavioral therapy, sedatives, etc.; such methods are known to the skilled artisan and described in Remington's Pharmaceutical Sciences by E. W. Martin. If desired, the first agent (e.g., one or more of anipamil, devapamil, falipamil, gallopamil, tiapamil, and verapamil) and/or the second agent (e.g., one or more of candesartan and telmisartan) is administered in combination with any conventional anti-anxiety therapy, including but not limited to, anxiolytic and/or sedative drugs, antipsychotics, mood stabilizers, anticonvulsants, antihistamines, and antidepressants.

The compositions of the present invention can be administered to a subject to treat a neuropsychological condition. The neuropsychological condition can be a brain and/or behavioral disorder. Non-limiting examples of brain and behavioral health disorders include affective disorders, anxiety disorders, neurodegenerative disorders, neurodevelopmental disorders, psychotic disorders, personality disorders, migraine disorders and somatoform disorders. Examples of affective disorders include bipolar disorder, cyclothymia, depression, dysthemia, generalized anxiety disorder, major depressive disorder, obsessive compulsive disorder, postpartum depression, post-traumatic stress disorder (PTSD), phobias, and seasonal affective disorder. Examples of anxiety disorders include panic disorder, social anxiety disorder, post-traumatic stress disorder, obsessive compulsive disorder and specific phobia. Examples of neurodegenerative disorders include Alzheimer's disease and Parkinson's disease. Examples of neurodevelopmental disorders include autism spectrum disorder, attention deficit hyperactive disorder (ADHD) and learning disorders. Examples of psychotic disorders include schizophrenia, schizoaffective disorder and major depression with psychosis. Examples of personality disorders include paranoid, schizoid, schizotypal, antisocial, borderline, histrionic, narcissistic, avoidant, dependent and obsessive-compulsive personality disorder. Examples of migraine-related disorders include migraine with aura, migraine without aura, acephalgic migraine, and basilar migraine. Examples of somatoform disorders include somatization disorder, hypochondriasis, conversion disorder, body dysmorphic disorder and chronic pain. The symptoms associated with the disease can be selected from one or more of the "ten cardinal symptoms" associated with brain and behavioral health disorders: anxiety, apathy, cognitive difficulty, depression, fatigue, headache, insomnia, irritability, body pain, and psychosis. Administration of a composition or dosage form of the present invention to a subject can reduce or ameliorate one or more of the symptoms associated with the bran and/or behavioral disorder.

The compositions of the present invention can be administered to a subject in an amount sufficient to alter regional cerebral blood flow in the subject. The cerebral regions can include one or more of the telencephalon, the diencephalon, and the mesencephalon. The compositions of the present invention can be administered to the subject in an amount sufficient to result in hemodynamic equilibrium in functional brain networks that coordinate among regions within the telencephalon, the diencephalon, and the mesencephalon in a subject.

Selection of Patients for Treatment

The present disclosure provides for the selection of patients who are likely to benefit from treatment with a therapeutic combination described herein. Such patients are selected as having a brain or behavior health disorders or a symptom thereof (e.g., anxiety, apathy, cognitive difficulty, depression, fatigue, headache, insomnia, irritability, body pain, and psychosis). Patients having a brain or behavior health disorders or a symptom thereof are selected for therapy with a combination therapeutic comprising a first agent selected from one or more of anipamil, devapamil, falipamil, gallopamil, tiapamil, and verapamil and a second agent that is one or more of candesartan and telmisartan.

Not being bound by theory, patients with the greatest energy supply/demand mismatch can have the greatest benefit from the compositions of the present disclosure. Patients with energy supply/demand mismatch can show the largest changes in functional connectivity before and after combination treatment. Four energy demand/supply phenotypes emerge when one considers energy as binary (high vs. low). The four types are: high demand/high supply (low risk of neuropsychiatric symptomatology), high demand/low supply (high risk of neuropsychiatric symptomatology), low demand/high supply (low risk of neuropsychiatric symptomatology), and low demand/low supply (low risk of neuropsychiatric symptomatology).

Kits or Pharmaceutical Systems

The present compositions can be assembled into kits or pharmaceutical systems for treating a brain or behavior health disorder or a symptom thereof (e.g., anxiety, migraine, depression, cognitive difficulty, anger, apathy, fatigue, pain, psychosis, or insomnia). Kits or pharmaceutical systems comprise a carrier means, such as a box, carton, tube or the like, having in close confinement therein one or more container means, such as vials, tubes, ampoules, bottles and the like. The kits or pharmaceutical systems can also comprise associated instructions for using the agents of the presently disclosed embodiments. In some embodiments, kits include the first agent (e.g., one or more of anipamil, devapamil, falipamil, gallopamil, tiapamil, and verapamil) and the second agent (e.g., one or more of candesartan and telmisartan).

The practice of the presently disclosed embodiments employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, can be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1: Novel Clinical Effects of Combination Treatment with Verapamil and Telmisartan—A Retrospective, Observational Cohort Study A study was completed to measure the novel clinical effects of compositions containing verapamil and telmisartan for treatment of neuropsychiatric symptomatologies in adults. The specific aims of this study were to describe 1) the magnitude of novel clinical effects on symptomatology; 2) the magnitude of novel clinical effects on psychosocial outcomes; and 3) the unique clinical effects that result from combination but not monotherapy treatment. For the main analysis, results were compared On vs. Off treatment across all patients.

Symptomatology On vs. Off Combination Treatment

Patients receiving combination treatment versus no treatment showed drastic reductions in overall symptomatology as measured by the sum of the ten cardinal disabling symptoms (i.e., anxiety, apathy, cognitive difficulty, depression, fatigue, headache, insomnia, irritability, body pain, and psychosis) and in 9/10 of the individual symptoms, including anxiety, depression, irritability, apathy, fatigue, body pain, insomnia, headache, and cognitive difficulty. All p-values were less than 0.001. All effect sizes were medium to large except effect sizes for depression and insomnia and headache which were small. Some effect sizes, including those for overall symptomatology, anxiety and apathy, were significantly large (above 1.0) (FIGS. 1A-1J).

Standardized Psychosocial Outcomes On and Off Treatment

Patients receiving combination treatment versus no treatment showed significant improvements in 6/10 of the standardized measures of psychosocial health, including General Life Satisfaction, Meaning & Purpose, Emotional Support, Instrumental Support, Friendship and Loneliness. All p-values were less than 0.1. All effect sizes were medium to large except for Meaning & Purpose (FIGS. 2A-2F).

Uniqueness of Combination Treatment vs. Individual Monotherapies

Figure 3A:
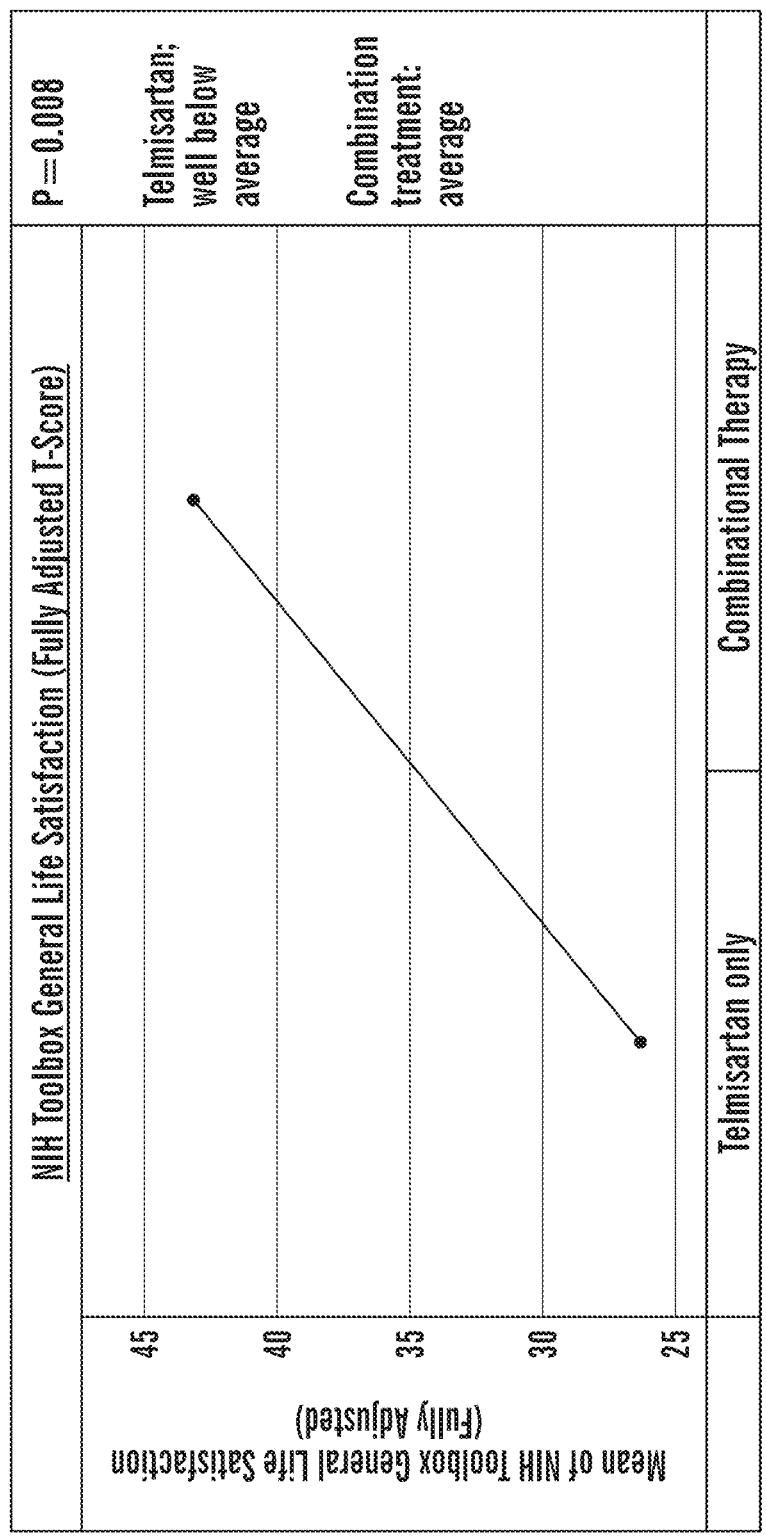
FIGS. 3A and 3B illustrate differences in outcomes between patients receiving the combination treatment and patients receiving only telmisartan.
Figure 3B:
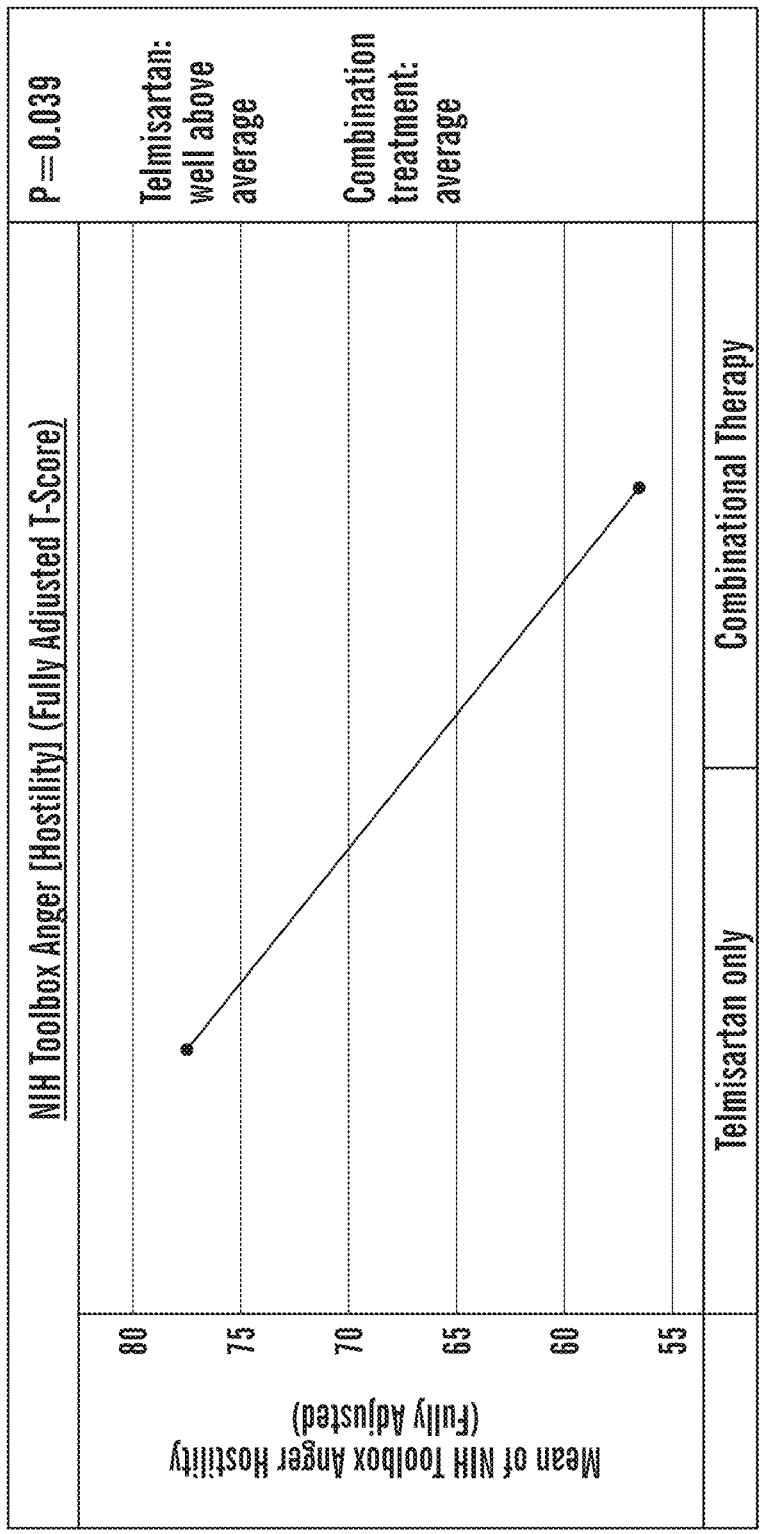

Outcomes from combination therapy were significantly different from outcomes from monotherapy with either telmisartan alone or with verapamil twice daily alone. Compared to the telmisartan only group, patients receiving combination treatment showed significantly improved outcome scores in NIH Toolbox measures of General Life Satisfaction ($p<0.01$) and Anger [Hostility] ($p<0.04$) (FIGS. 3A-3B).

Figure 4A:
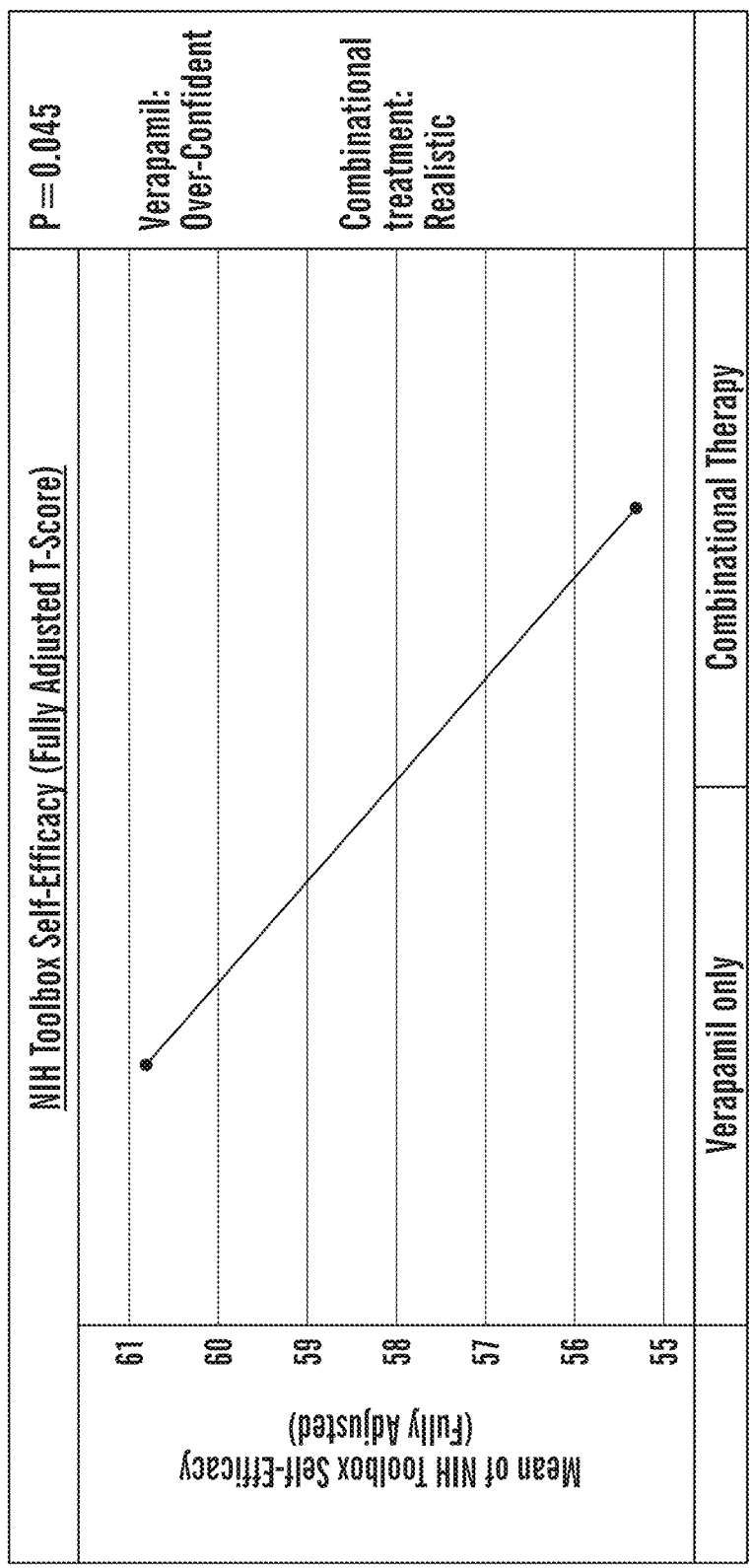
FIGS. 4A and 4B illustrate differences in outcomes between patients receiving the combination treatment and patients receiving only verapamil.
Figure 4B:
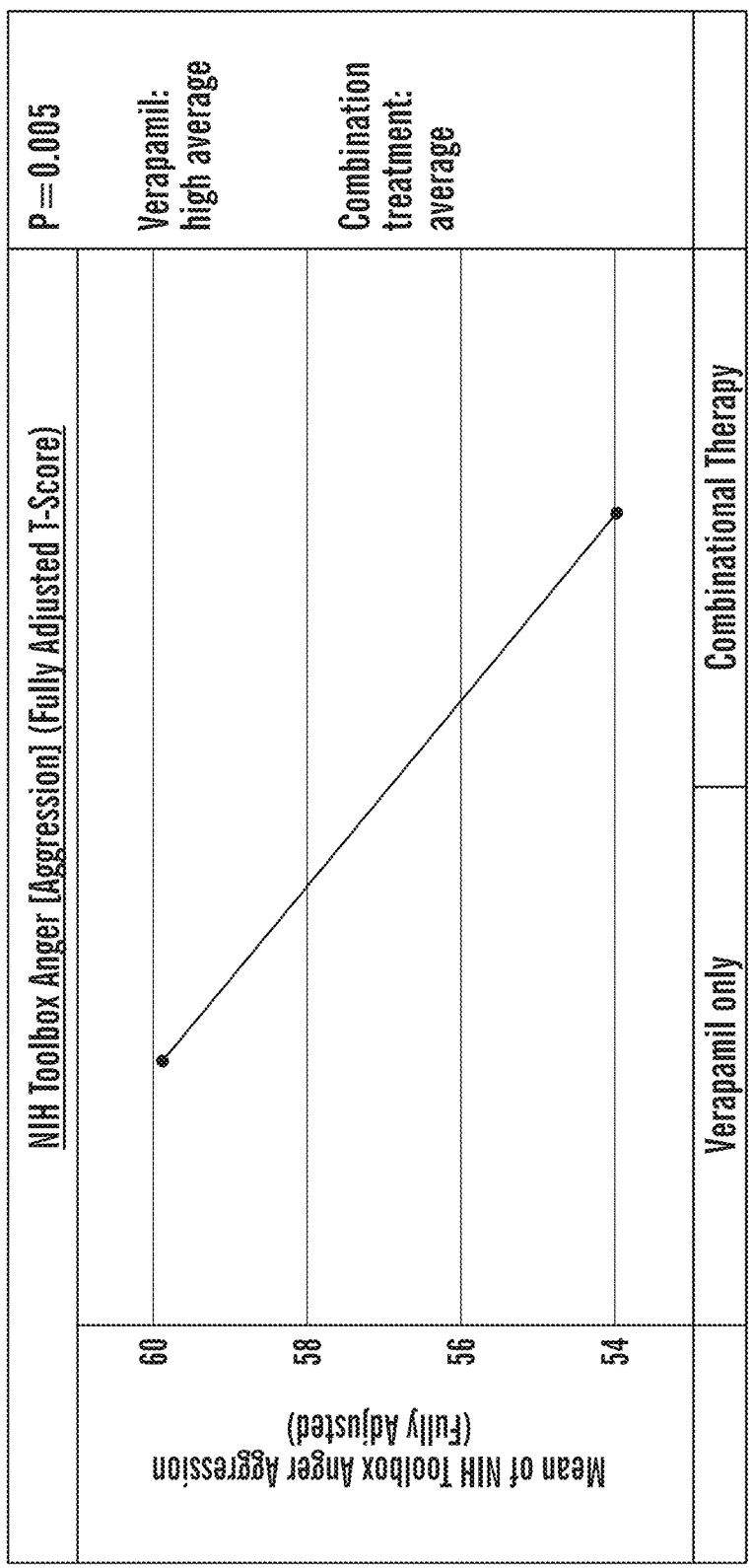

Compared to the verapamil group, patients receiving combination treatment showed significantly different scores in NIH Toolbox measures of NIH Toolbox Self-Efficacy ($p<0.05$) and Anger [Aggression] ($p<0.06$) (FIGS. 4A-4B).

Example 2: An Observational Cohort Study of Compositions Containing Verapamil and Telmisartan, a Novel Combination Treatment for Neuropsychiatric Symptomatology in Adults An observational cohort study was completed to evaluate the safety and efficacy of compositions containing verapamil and telmisartan for treatment of neuropsychiatric symptomatologies in adults. The specific aims of this study were to 1) measure the safety of combination treatment, 2) compare efficacy of combination treatment across different symptoms and for patients with different disorders; and 3) use a physiological measure (the Weber test) to test whether the mechanism of action of the combination of treatment results in the normalization of functional connectivity in the auditory functional network. For the main analysis, results were compared before and after treatment in the same patient.

Demographics

A total of 102 patients received combination therapy and consented to the CEDAR study (Protocol Number: CEDAR2017 originally approved by Aspire IRB on Apr. 11, 2017). Demographic details as well as information on handedness, primary diagnosis, pre-existing medications, and presence of cardiovascular diagnosis can be found in Table 2.

TABLE 2

| Baseline Demographics | |
|---|---|
| Characteristic | Baseline (n = 102) |
| Age (SD) | 46.0% (14.0) |
| Gender | |
| Male | 57.8% (59) |
| Female | 42.2% (43) |

TABLE 2-continued

Baseline Demographics

| Characteristic | Baseline (n = 102) |
|---|---|
| Race | |
| White or Caucasian | 82.4% (84) |
| African or black | 15.7% (16) |
| Asian | 1.0% (1) |
| Mixed | 1.0% (1) |
| Education | |
| Less than High School | 11.1% (11) |
| High School, GED, or equivalent | 23.2% (23) |
| Associate's or some college | 36.4% (36) |
| Bachelor's | 18.2% (18) |
| Master's and above | 11.2% (11) |
| Handedness | |
| Right | 71.1% (69) |
| Left | 7.2% (2) |
| Ambidextrous | 21.7% (21) |
| Primary Diagnosis | |
| Panic Disorder | 19.6% (20) |
| PTSD | 11.8% (12) |
| Chronic Pain syndrome | 5.9% (6) |
| Other | 63.5% (64) |
| Pre-existing medications | |
| Anti-depressants | 40.3% (31) |
| Benzodiazepines | 37.7% (29) |
| Stimulants | 18.2% (14) |
| Opiates | 39.2% (29) |
| Anti-psychotics | 15.6% (12) |
| Mood stabilizers | 18.2% (14) |
| Prior Cardiovascular Diagnosis | 33.7% (35) |

Self-Report Neuropsychiatric Symptomatology

Patients receiving combination treatment showed significant reductions in symptomatology across eight out of 10 of the cardinal disabling symptoms (other than fatigue and psychosis); the greatest effects were seen for apathy, anxiety, cognitive difficulty and overall neuropsychiatric disability (see Table 3).

In patients with high anxiety at baseline (7 or above), patients receiving combination treatment showed significant reductions in symptomatology across nine out of 10 of the cardinal disabling symptoms. Effect sizes were large for anxiety, irritability, apathy and overall neuropsychiatric disability, medium for depression, insomnia, and cognitive difficulty and small for all remaining symptoms (fatigue, pain and headache) (see Table 4). In patients with moderate anxiety at baseline (4 or above), effect sizes were medium for anxiety, apathy, cognitive disturbance and overall neuropsychiatric disability and small for all remaining symptoms besides psychosis (see Table 5).

In patients with high baseline cognitive difficulty (7 or above), effect sizes were large for apathy, cognitive difficulty and overall neuropsychiatric disability, medium for anxiety, depression, and irritability, and small for anxiety, body pain and insomnia (see Table 6). In patients with moderate baseline cognitive difficulty (4 or above), effect sizes were large for cognitive difficulty, medium for anxiety, depression, irritability, apathy and overall neuropsychiatric disability, and small for fatigue and insomnia (See Table 7).

TABLE 3

Effect of Combination Treatment on Self-Reported Neuropsychiatric Symptomatology (Last observation mean follow-up was 8.9 months)

| | Baseline (n = 77) | First Observation | P-value | Cohen's | Baseline (n = 61) | Last Observation | P-value | Cohen's |
|---|---|---|---|---|---|---|---|---|
| Anxiety | 5.6 | 4.5 | 0.0020* | 0.39 | 5.4 | 4.1 | 0.0017* | 4.44 |
| Depression | 4.7 | 4.1 | 0.1007 | 0.19 | 4.6 | 3.6 | 0.0328* | 0.28 |
| Irritability | 4.4 | 3.6 | 0.0563 | 0.25 | 4.2 | 3.4 | 0.0481* | 0.27 |
| Apathy | 4.8 | 3.3 | 0.0002* | 0.49 | 4.6 | 3.1 | 0.0017* | 0.47 |
| Fatigue | 4.6 | 4.0 | 0.1004 | 0.19 | 4.4 | 3.9 | 0.1080 | 0.19 |
| Body pain | 4.8 | 4.2 | 0.1523 | 0.08 | 5.0 | 4.1 | 0.0103* | 0.29 |
| Insomnia | 4.5 | 3.8 | 0.0703 | 0.21 | 4.4 | 3.4 | 0.0257 | 0.31 |
| Headache | 3.0 | 2.5 | 0.1178 | 0.16 | 3.1 | 2.2 | 0.4091* | 0.29 |
| Psychosis | 0.9 | 0.9 | 0.9563 | −0.01 | 0.9 | 0.8 | 0.5942 | 0.05 |
| Cognitive Disability | 5.1 | 3.9 | 0.0023* | 0.37 | 4.9 | 3.7 | 0.0032* | 0.41 |
| Neuropsychiatric Disability | 42.4 | 34.6 | 0.0033* | 0.34 | 41.6 | 32.2 | 0.0008* | 0.41 |

TABLE 4

Self-report Symptomatology in Patients with Baseline Severe Anxiety Before and After Combination Treatment

| | Baseline (n = 34) | First Observation | P-value | Cohen's |
|---|---|---|---|---|
| Anxiety | 8.1 | 5.1 | 0.0000* | 1.24 |
| Depression | 6.6 | 4.7 | 0.0031* | 0.54 |
| Irritability | 6.7 | 4.4 | 0.0015* | 0.75 |
| Apathy | 6.2 | 3.9 | 0.0002* | 0.71 |
| Fatigue | 6.0 | 4.7 | 0.0283* | 0.41 |
| Body pain | 5.8 | 4.8 | 0.0204* | 0.27 |
| Insomnia | 6.4 | 4.6 | 0.0031* | 0.56 |
| Headache | 4.0 | 2.6 | 0.0298* | 0.44 |
| Psychosis | 1.5 | 1.3 | 0.7103 | 0.06 |
| Cognitive Disability | 6.4 | 4.5 | 0.0009* | 0.59 |
| Neuropsychiatric Disability | 57.8 | 40.4 | 0.0000* | 0.74 |

TABLE 5

Self-report Symptomatology in Patients with Baseline Moderate Anxiety Before and After Combination Treatment

| | Baseline (n = 60) | First Observation | P-value | Cohen's |
|---|---|---|---|---|
| Anxiety | 6.8 | 5.1 | 0.0001* | 0.67 |
| Depression | 5.8 | 4.6 | 0.0124* | 0.36 |
| Irritability | 5.4 | 4.1 | 0.0127* | 0.41 |
| Apathy | 5.5 | 3.6 | 0.0000* | 0.64 |
| Fatigue | 5.5 | 4.5 | 0.0267* | 0.33 |
| Body pain | 5.5 | 4.6 | 0.0495* | 0.25 |
| Insomnia | 5.4 | 4.3 | 0.0276* | 0.30 |
| Headache | 3.4 | 2.4 | 0.0274* | 0.30 |
| Psychosis | 1.1 | 1.0 | 0.7403 | 0.04 |
| Cognitive Disability | 5.8 | 4.2 | 0.0005* | 0.51 |
| Neuropsychiatric Disability | 50.0 | 38.4 | 0.0001* | 0.56 |

TABLE 6

Self-report Symptomatology in Patients with Baseline Severe Cognitive Disturbance Before and After Combination Treatment

| | Baseline (n = 32) | First Observation | P-value | Cohen's |
|---|---|---|---|---|
| Anxiety | 6.9 | 5.8 | 0.0348* | 0.42 |
| Depression | 6.8 | 5.0 | 0.0041* | 0.62 |
| Irritability | 6.2 | 4.5 | 0.0142* | 0.54 |
| Apathy | 6.4 | 3.7 | 0.0000* | 0.93 |
| Fatigue | 6.1 | 5.2 | 0.1311 | 0.36 |
| Body pain | 6.5 | 5.2 | 0.0423* | 0.40 |
| Insomnia | 6.4 | 5.0 | 0.0206* | 0.42 |
| Headache | 3.6 | 3.4 | 0.7878 | 0.06 |
| Psychosis | 1.3 | 1.4 | 0.8933 | 0.02 |
| Cognitive Disability | 8.3 | 5.3 | 0.0000* | 1.26 |
| Neuropsychiatric Disability | 58.6 | 44.5 | 0.0015* | 0.71 |

TABLE 7

Self-report Symptomatology in Patients with Baseline Moderate Cognitive Disturbance Before and After Combination Treatment

| | Baseline (n = 51) | First Observation | P-value | Cohen's |
|---|---|---|---|---|
| Anxiety | 6.4 | 5.0 | 0.0019* | 0.50 |
| Depression | 6.0 | 4.4 | 0.0014* | 0.49 |
| Irritability | 5.7 | 4.1 | 0.0027* | 0.50 |
| Apathy | 5.5 | 3.6 | 0.0005* | 0.61 |
| Fatigue | 5.5 | 4.5 | 0.0407* | 0.34 |
| Body pain | 5.9 | 4.9 | 0.0683 | 0.29 |
| Insomnia | 5.5 | 4.1 | 0.0111* | 0.36 |
| Headache | 3.6 | 2.7 | 0.1090 | 0.30 |
| Psychosis | 1.3 | 1.1 | 0.6420 | 0.06 |
| Cognitive Disability | 7.0 | 4.5 | 0.0000* | 0.90 |
| Neuropsychiatric Disability | 52.3 | 39.1 | 0.0001* | 0.62 |

NIH Toolbox Standardized Outcome Measures

NIH Toolbox measurements showed significant improvements in general life satisfaction and borderline significant improvements in social satisfaction (Table 8). Outcomes with smaller sample sizes including processing speed (n=17) and dimensional change card sort (n=18) showed no significant changes before and after treatment (see Table 8).

TABLE 8

NIH Toolbox Standardized Outcome Measures

| | Baseline | First Observation | P-value | Cohen's |
|---|---|---|---|---|
| Processing Speed (n = 18) | 39.3 | 49.7 | 0.8170 | 0.16 |
| Dimensional Change Card (n = 17) | 54.2 | 56.9 | 0.3550 | 0.19 |
| General Life Satisfaction (n = 41) | 37.6 | 41.5 | 0.0212* | 0.34 |
| Meaning and Purpose (n = 42) | 39.4 | 41.3 | 0.1743 | 0.19 |
| Social Satisfaction (n = 41) | 35.6 | 38.1 | 0.0941 | 0.22 |

Weber Lateralization Showing Bi-directional Changes of Observations of Sensorineural Function The Weber test is a common clinical examination technique that a physician can use to identify sensorineural hearing loss. The Weber test employs a tuning fork, which is placed in the center of the upper forehead, with a prompt asking the patient to report whether the sound lateralizes to the left or to the right. In a patient with sensorineural hearing loss, the sound lateralizes to the stronger side. Patients with neuropsychiatric disorders (e.g., brain and/or behavioral health disorders) without sensorineural hearing loss frequently report lateralization to the left or right when tested with the Weber test. This lateralization could be due to the fact that, in fact, auditory functional networks can be left-, right- or bilaterally dominant (Asymmetries of the planum temporale and Heschl's gyrus: relationship to language lateralization. Dorsaint-Pierre R, Penhune V B, Watkins K E, Neelin P, Lerch J P, Bouffard M, Zatorre R J. Brain. 2006 May; 129(Pt 5):1164-76. doi: 10.1093/brain/aw1055. Epub 2006 Mar. 14).

Figure 7:
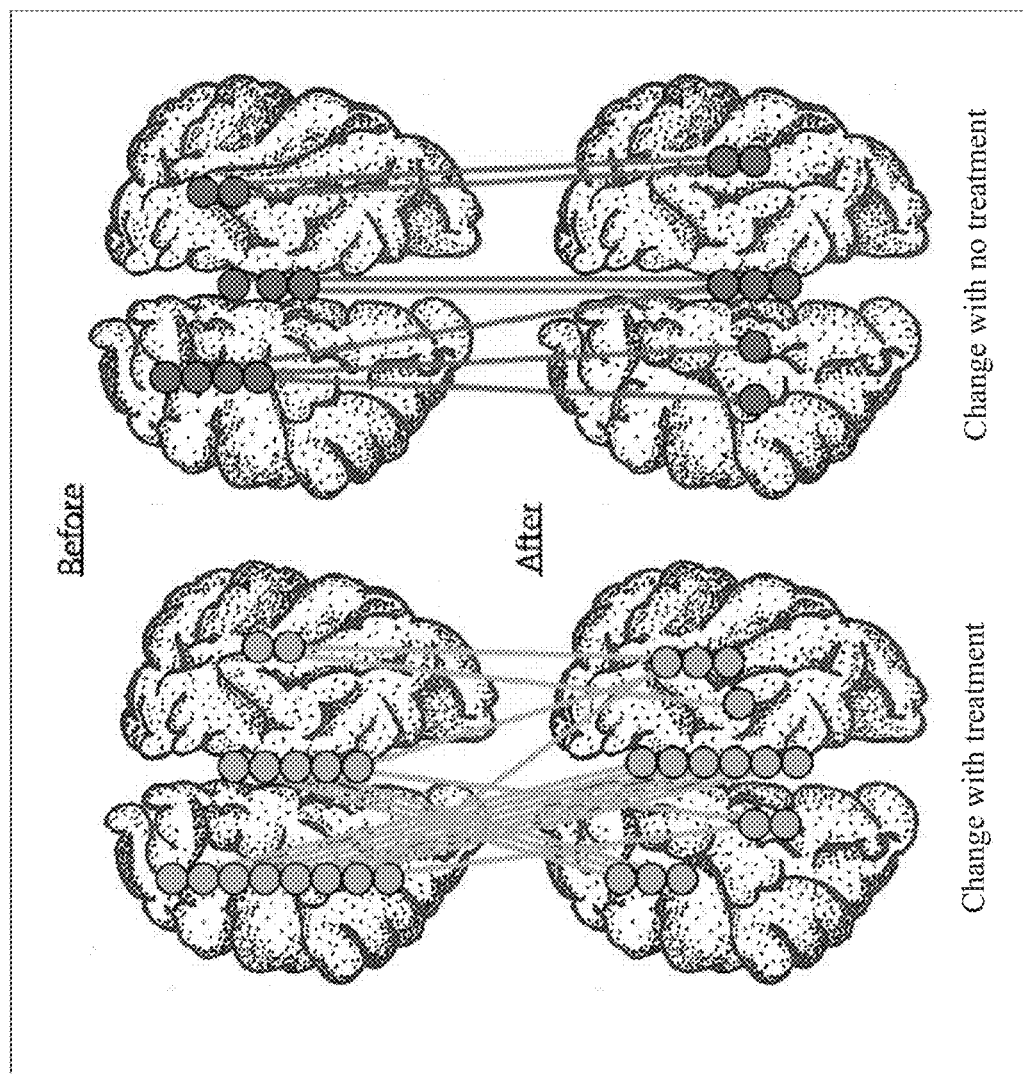
FIG. 7 is a diagram showing bidirectional changes in Weber lateralization in patients who either start, stop or change dose of a composition containing verapamil and telmisartan. Of the individuals that had a change in treatment, 83% (15/18) had a change in their Weber lateralization. Of those that had no change in treatment, 20% (1/5) reported a change in Weber lateralization. This difference in Weber lateralization changes between patients who had vs. did not have a change in treatment was statistically significant ($p=0.006$).

FIG. 7 shows changes in Weber lateralization in patients who either started, stopped or changed dose of a composition containing verapamil and telmisartan. These changes were not present at visit intervals during which the composition dose remained stable. Remarkably, in some patients, the Weber result corrected towards the left while, in other patients, the Weber result corrected towards the right.

For a total of 23 patients, Weber test results were available both before and after treatment (see Table 9). 15 out of 18 patients who had a treatment change showed a lateralization change, whereby only one out of five patients who had no treatment change showed a lateralization change. This difference was statistically significant (p<0.006).

TABLE 9

Weber lateralization in patients On vs. Off Combination Treatment
. tab Latchange Txchange, chi2

| Lat change | Tx change no | yes | Total |
|---|---|---|---|
| no | 4 | 3 | 7 |
| yes | 1 | 15 | 16 |
| Total | 5 | 18 | 23 |

Pearson chi2(1) = 7.4134 Pr = 0.006

Bidirectional Changes in Blood Pressure

Figure 8:
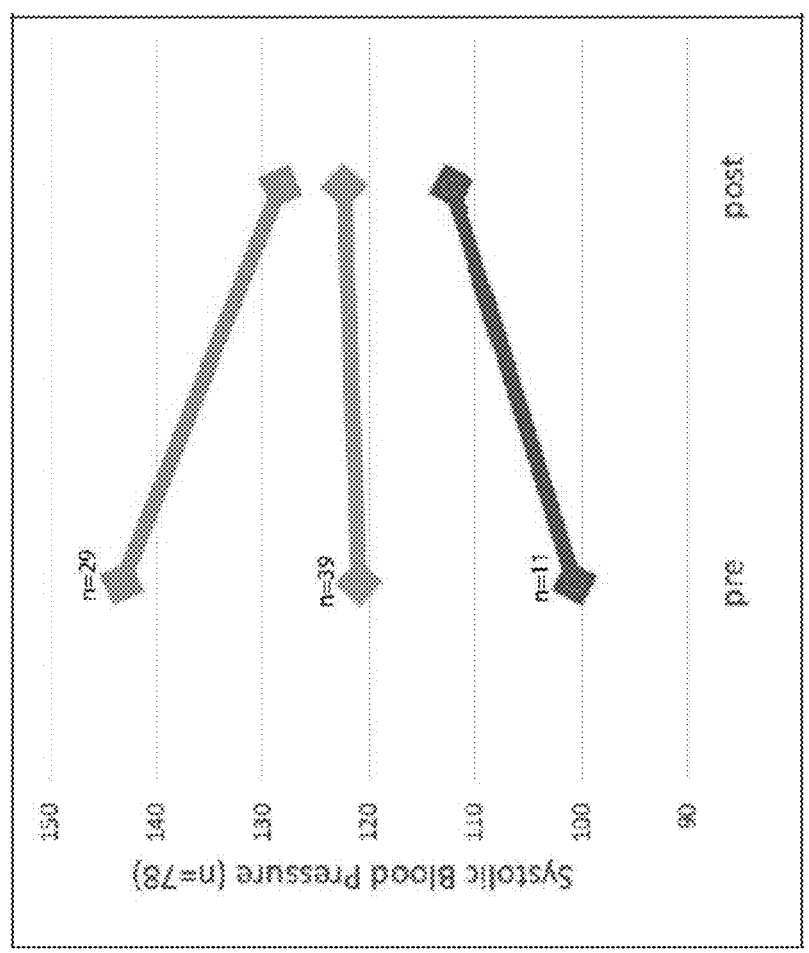
FIG. 8 is a plot showing bi-directional influences of a composition containing verapamil and telmisartan on patient blood pressure. For the 29 patients with high blood pressure, the pre-post decrease to within normal range was statistically significant ($p=0.0001$). For the 11 patients with low blood pressure, the pre-post increase to within normal range was statistically significant ($p=0.001$). For the 29 patients with normal blood pressure, the pre-post change was not statistically significant ($p=0.553$).
Figure 9:
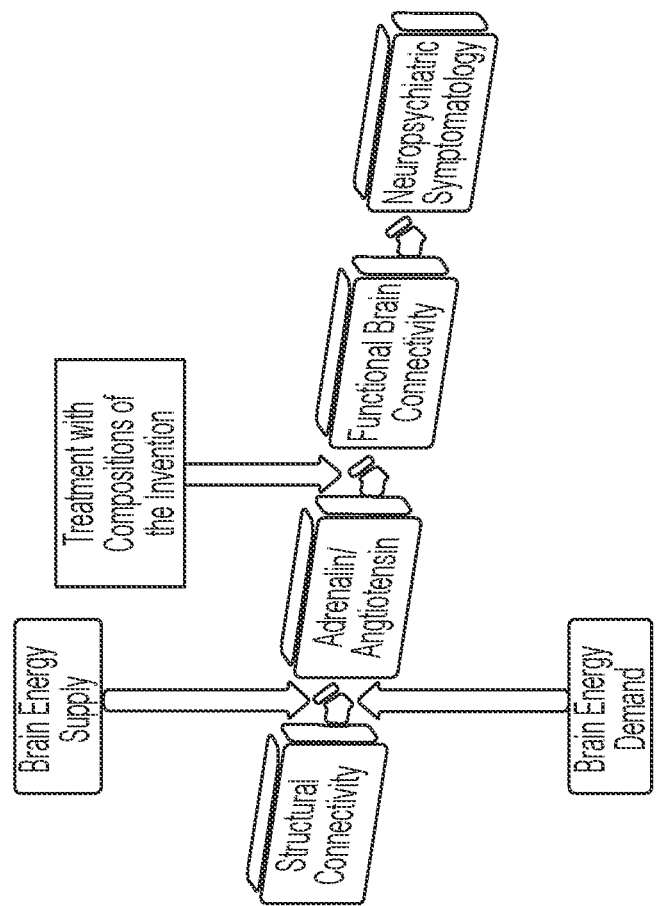
FIG. 9 is a diagram presenting a proposed method by which compositions of the present invention comprising a first agent selected from one or more of anipamil, candesartan, devapamil, falipamil, gallopamil, telmisartan, tiapamil, and verapamil and a second agent selected from one or more of candesartan and telmisartan can affect dynamic changes caused by psychological stress. Depending on the structural make-up of the brain, psychological stress can cause the body to respond with dynamic adaptations in adrenalin and angiotensin, especially in settings of brain energy supply/demand mismatches. These adaptations cause changes in functional connectivity of the brain, which modulates metabolic demand in selectively vulnerable brain regions. In the presence of the compositions, the dynamic changes cause by psychological stress on functional connectivity are regulated, which results in lower neuropsychiatric symptomatology.

In patients with high blood pressure at baseline, administration of the composition containing verapamil and telmisartan was associated with decreases to normal levels. In patients with low blood pressure at baseline, administration was associated with increases to normal levels. In patients with normal blood pressure at baseline, treatment was not associated with any significant changes. The bi-directional changes suggest regulation of functional connectivity in mesencephalic brain regions that mediate autonomic balance. (FIG. 8)

Significant Differences in Social Outcomes in Patients on Combination vs. Monotherapy Chi-squared analysis was performed to compare the proportions of patients on combination therapy who reported significant social changes vs. patients on monotherapy (Table 10). At each visit, patients were systematically assessed with self-report questions that addressed basic human needs related to Love & Belonging. Results showed that patients with combination therapy were significantly more likely to report changes in social momentum, new social contacts, dress, and appearance. Without being bound by theory, these social changes result from changes in functional brain networks related to social cognition that rely heavily on brain regions within the diencephalon and telencephalon.

TABLE 10

Comparison of the proportions of patients on combination therapy who reported significant social changes vs. patients on monotherapy.

| Outcome Measure | N | P-value (Combination Therapy vs. Monotherapy)* |
|---|---|---|
| Level 3: Love & Belonging | | |
| I have momentum with respect to my social life. | 21 | 0.019 |
| I have been dressing more or less formally. | 35 | 0.017 |
| I have been dressing with more or less color. | 35 | 0.006 |
| Since my last visit, I cut or colored my hair. | 29 | 0.036 |
| Since my last visit, I've been meeting new people. | 21 | 0.038 |

*Monotherapy refers to telmisartan only or verapamil only

Discussion

A clinical study was completed in humans using a combination of verapamil with telmisartan to treat neuropsychiatric indications (e.g., brain and/or behavioral health disorders). This observational study was motivated by clinical impressions of remarkable symptomatic improvement in patients with several common neuropsychiatric co-morbidities who were treated serendipitously with combination therapy for approximately one year as part of real-world care to achieve more complete relief. The study was designed to empirically test, within the limits of an observational study design, the safety and effectiveness of combination treatment when delivered in the context of routine neuropsychiatric care. Most patients received combination treatment augmented to standard of care therapies.

In 102 patients, neither systolic nor diastolic blood pressure was significantly different after combination treatment, despite significant improvements in apathy, anxiety, cognitive difficulty and overall neuropsychiatric disability (e.g., a brain and/or behavioral health disability). Rates of adverse medical symptomatology did not change significantly before and after treatment. The adverse symptom profile of combination treatment resembled the established adverse symptom profiles of telmisartan and verapamil. Standardized testing, before and after, showed significant improvements in General Life Satisfaction.

Observational studies can provide similar estimates of effect sizes as compared to randomized, controlled trials (Development and reliability testing of a cross-cutting symptom assessment for DSM-5. American Journal of Psychiatry, 170(1), 59-70. Narrow, W. E., Clarke, D. E., Kuramoto, S. J., Kraemer, H. C., Kupfer, D. J., Greiner, L., & Regier, D. A. (2013). DSM-5 field trials in the United States and Canada, Part III). This study includes several strengths that support the accuracy of effect sizes noted. These include the large sample size, the longitudinal study design allowing for analysis of temporal effects, the long duration of follow-up, the inclusion of patients with multiple co-morbidities (which more accurately resembles real-world care), the inclusion of objective measures such as vital signs, and NIH Toolbox measures. Another strength of the study was the number of different analyses performed to test association vs. causation as per Bradford Hill Criteria. In order for a factor to be considered causative vs. associative, the following criteria should be observed: strength, consistency, specificity, temporality, biological gradient, plausibility, coherence, experiment, analogy and reversibility.

Not wishing to be bound by theory, combination treatment is acting on central pathways that are common to more than one neuropsychiatric disorder (e.g., a brain and/or behavioral health disorder). Without intending to be bound by theory, the unique combination of angiotensin II receptor blockade with concomitant adrenergic blockade leads to more balanced distribution in cerebral blood flow particularly in the diencephalon, which is the region of the brain important for social and emotional awareness. In other words, by influencing cognition (telencephalon) simultaneously with emotion (mesencephalon), this synergy can result in improved social cognition (diencephalon). This hypothesis is based on findings of conspicuous social changes in patients who took combination therapy. For example, changes were observed in social and dressing behavior in patients taking combination treatment. The results of the study showed an improvement in social satisfaction in patients on combination treatment. This is further supported by analyses of results from the Weber test, performed as part of routine visits, which measures lateralization of the brain's auditory functional network. In the clinic, patients who initiated combination treatment or changed from monotherapy to combination treatment displayed shifts from one visit to the next in lateralization of the Weber test. Shifts in lateralization of the Weber test do not occur with standard of care medications.

Not wishing to be bound by theory, the composition containing verapamil and telmisartan can serve a regulatory function in brain regions associated with the auditory functional network. Since these changes in auditory function correlated with clinical improvements in social function, the composition can affect not only auditory function, but also the interoceptive/exteroceptive awareness as well as the social communication that rely on auditory functioning. In fact, the auditory cortex participates directly in networks for emotional processing (disability and poor quality of life associated with comorbid anxiety disorders and physical conditions. Sareen J, Jacobi F, Cox B J, Belik S L, Clara I, Stein M B. Arch Intern Med. 2006 Oct. 23; 166(19):2109-16. doi: 10.1001/archinte.166.19.2109).

METHODS OF THE EXAMPLES

The following methods were used in Example 1.
Data and Combination Therapy

Data for this study was selected from the Comparative Effectiveness Dementia and Alzheimer's Registry (CEDAR) Project. The CEDAR Project is an IRB-approved, observational study of real-world care for patients seeking treatment for any neurological, psychological or psychiatric condition at a community-based neuropsychiatry specialty practice in Broward County, FL. Patients received their usual course of care, which included medication adjustment and routine cognitive behavioral therapy for neurological, psychiatric and psychological co-morbidities. Treatment was not altered as a result of participation in the observational study. Only patients who consented to the CEDAR project were included in this study.

The combination therapy comprised administering either 120 mg or 180 mg of verapamil twice per day and either 40 mg or 80 mg of Telmisartan twice per day. Control groups used for comparison received no amount of either of verapamil and telmisartan, or only telmisartan, or only verapamil.

Demographics

Data from a total of 76 patients who consented to the Comparative Effectiveness Dementia and Alzheimer's Registry (CEDAR) study was analyzed. Average age, gender, ethnicity and education from each treatment group is provided in Table 11.

TABLE 11

| | | | Biological Gender | | Gender Count | Education | | | | | |
|---|---|---|---|---|---|---|---|---|---|---|---|
| | | Age Mean | Not Reported Count | Male Count | | Not Reported Count | Some middle and/or high school Count | Some elementary school Count | Some college Count | Master's Degree Count | JD Count |
| Treatment Group | Neither | 43.26 | 2 | 80 | 50 | 0 | 29 | 1 | 39 | 8 | 3 |
| | Telmisartan only | 45.80 | 0 | 72 | 23 | 0 | 2 | 0 | 56 | 6 | 0 |
| | Verapamil only | 41.37 | 6 | 39 | 25 | 0 | 10 | 2 | 14 | 11 | 2 |
| | telmisartan once daily and verapamil once daily | 46.52 | 0 | 19 | 10 | 0 | 2 | 0 | 14 | 0 | 0 |
| | telemisartan twice daily and verapamil twice daily | 46.83 | 0 | 103 | 83 | 0 | 17 | 0 | 83 | 12 | 3 |

| | | Comparisons of Column Proportions[c] | | | | | | | | | |
|---|---|---|---|---|---|---|---|---|---|---|---|
| | | Biological Gender | | | Education | | | | | | |
| | | Not Reported (A) | Male (B) | Gender (C) | Not Reported (A) | Some middle and/or high school (B) | Some elementary school (C) | Some college (D) | Master's Degree (E) | JD (F) | High school graduate (G) |
| Treatment Group | Neither | | | | .[a,b] | D( .000) I( .004) | | | | | D( .019) |
| | Telmisartan only | .[a] | C( .002) | | .[a,b] | | .[a] | B( .001) G( .001) | | .[a] | |

TABLE 11-continued

|  |  |  |  |  |  |  |  |  |  |  |  |
|---|---|---|---|---|---|---|---|---|---|---|---|
| | Verapamil only | B( .000) C( .000) | | .a,b | | D( .004) I( .033) | D( .001) I( .044) | | | | D( .023) |
| | telmisartan once daily and verapamil once daily | .a | | .a,b | | .a | | | .a | | .a |
| | telemisartan twice daily and verapamil twice daily | .a | B( .017) | .a,b | | .a | | | | | |

| | | | | | | | Race | | | | Ethnicity | | |
|---|---|---|---|---|---|---|---|---|---|---|---|---|---|
| | | High school graduate Count | GED or equivalent Count | Bachelor's Degree Count | Associate degree Count | Not Reported Count | White or Caucasian Count | African or Black Count | Asian Count | Mixed Count | Not Reported Count | Not Hispanic or Latino Count | Hispanic or Latino Count |
| Treatment Group | Neither | 24 | 3 | 21 | 2 | 2 | 90 | 33 | 4 | 3 | 11 | 107 | 14 |
| | Telmisartan only | 2 | 0 | 26 | 3 | 0 | 67 | 28 | 0 | 0 | 17 | 56 | 22 |
| | Verapamil only | 13 | 1 | 9 | 2 | 6 | 41 | 21 | 0 | 2 | 13 | 50 | 7 |
| | telmisartan once daily and verapamil once daily | 4 | 0 | 8 | 1 | 0 | 21 | 8 | 0 | 0 | 1 | 22 | 6 |
| | telemisartan twice daily and verapamil twice daily | 16 | 4 | 43 | 8 | 0 | 142 | 39 | 2 | 3 | 30 | 134 | 22 |

| | | | | | Race | | | | | Ethnicity | | |
|---|---|---|---|---|---|---|---|---|---|---|---|---|
| | | GED or equivalent (H) | Bachelor's Degree (I) | Associate degree (J) | Not Reported (A) | White or Caucasian (B) | African or Black (C) | Asian (D) | Mixed (E) | Not Reported (A) | Not Hispanic or Latino (B) | Hispanic or Latino (C) |
| Treatment Group | Neither | | | | | | | | | A( .048) | | |
| | Telmisartan only | .a | B( .008) G( .009) | | .a | | | .a | .a | | | B( .004) |
| | Verapamil only | | | | B( .000) C( .000) | | | .a | | | | |
| | telmisartan once daily and verapamil once daily | .a | | | .a | | | .a | .a | | | |

TABLE 11-continued telemisartan twice daily and verapamil twice daily .[a]

Results are based on two-sided tests.
For each significant pair, the key of the category with the smaller column proportion appears in the category with the larger column proportion.
Significance level for upper case letters (A, B, C): .05
[a]This category is not used in comparisons because its column proportion is equal to zero or one.
[b]This category is not used in comparisons because the sum of case weights is less than two.
[c]Tests are adjusted for all pairwise comparisons within a row of each innermost sub-table using the Bonferroni correction.

Diagnosis and Medical Complexity

Clinical diagnoses were made by a neurologist with behavioral neurology fellowship training using independent medical record review complete neurological history and exam, a self-reported psychosocial assessment adapted for the neuropsychiatry population based on Maslow's hierarchy of needs, and DSM-V Psychiatric diagnostic interview. Medical complexity was scaled using a composite score that summarized positive affirmations (one point each) to a series of questions about prior medical, surgery and family history.

Symptomatology and Disability

The National Institute of Health (NIH) Toolbox was used to collect primary outcomes in cognitive, emotional and psychosocial domains. These measures were chosen because they were designed specifically to provide valid, longitudinal assessment of neuropsychiatric symptoms in community-based populations for children, adults, and elderly.

The primary outcomes included standardized and self-report measures of patients while on and off treatment. The NIH Toolbox Pattern Comparison Processing Speed and Dimensional Change Card Sort test fully adjusted T-scores were the primary cognitive outcomes. The NIH Toolbox Negative Affect Composite Score and the NIH Toolbox Psychological Well-Being Composite Score were the primary emotional and psychosocial outcomes. The Negative Affect Composite Score measures individual components of fear, anger and sadness. The Psychological Well-Being Composite Score measures individual components of positive affect, general life satisfaction, meaning & purpose, perceived stress, self-efficacy, emotional support, instrumental support, loneliness, hostility, perceived rejection and perceived hostility. To measure self-report symptom severity, a scale of average symptom severity across all ten cardinal symptoms (i.e., anxiety, apathy, cognitive difficulty, depression, fatigue, headache, insomnia, irritability, pain (e.g., body pain), and psychosis), individually measured from 0 to 10, and collectively summarized from 0 through 100 scale, difficulty on a scale of 0 through 10 as reported by the patient over the course of clinical care was also used as a primary outcome.

Exploratory outcomes measured psychosocial advancement including changes in social support, social behavior, relationships, career standing, and housing status, were measured by self-report, using the total number of self-reported positive versus negative psychosocial events over the course of treatment.

The medical safety of the treatment was assessed via measurement of medical symptomatology, as assessed by a self-report scale of the total number of positively reported symptoms before and after treatment using a patient self-report to a review of systems battery, which asks specifically about each body system one at a time and is administered at each visit as part of routine care. Blood pressure and pulse and medication adherence data were collected from clinical assessments performed as part of routine care.

Statistics

To measure the overall effect of combination treatment on and off treatment, a within-group comparison of means was performed for patients in the following treatment groups: No treatment, monotherapy (verapamil only or telmisartan only), and combination therapy (verapamil plus telmisartan). Since the data consists of multiple, repeated visits whereby patients were either on or off therapy with one or the other medication, an average of all visits off of medication was used to measure "Off Treatment" outcomes for patients. An average of all visits on medication was used to measure "On Treatment" outcomes. Effect sizes were calculated using Cohen's methodology and quantified using standard ranges signifying small (0.2 to 0.5), medium (0.5 to 0.8) or large (above 0.8) effects of treatment.

To measure the specific effect of individual components of the combination treatment versus the combination treatment, a between-group post-hoc analysis of variance was performed for patients in the following treatment groups: No treatment, treatment with verapamil only, treatment with telmisartan only, and treatment with combination therapy (verapamil plus telmisartan).

The following methods were used in Example 2.

Patient Population

Data for this study was selected from the neuro well FREE Not for Profit Corporation's Comparative Effectiveness Dementia & Alzheimer's Registry (CEDAR) Project. The CEDAR Project is an IRB-approved, observational study of real-world care for patients seeking treatment for any Neurological, Psychological or Psychiatric condition at a community-based Neuropsychiatry specialty practice in Broward County, FL. The practice accepts all major health insurances and accepts people of all ages and all diagnoses. Patients received their usual course of care, which included medication adjustment and routine cognitive behavioral therapy for neurological, psychiatric and psychological co-morbidities. Treatment was not altered as a result of participation in the observational study. Only patients who consented to the CEDAR project were included in this study.

Demographics & Diagnoses

Demographic details, medical history, and exam were collected at the initial visit as part of a comprehensive initial neuropsychiatric evaluation. A comprehensive psychosocial assessment modeled after Maslow's Hierarchy of Needs was delivered to all patients at baseline. A clinical diagnosis was made by a neurologist with Behavioral Neurology fellowship training using a DSM-V based Psychiatric diagnostic interview.

Safety

Vital signs were measured using systolic, diastolic blood pressure and pulse measurements that were collected as part of routine care. Adverse events were measured using a ten-point review of systems inventory covering Constitutional, HEENT, Respiratory, Gastrointestinal, Genitourinary, Dermatology, Musculoskeletal, Endocrine, Neurology, and Psychiatry symptoms. A point of 1 was given for each symptom reported as present, for a total possible score of 93.

To calculate the rate of adverse events on combination therapy, the percentage of people who responded "Yes" to one of the symptoms at the first month of treatment was calculated for each of the symptoms.

Effectiveness

Symptom severity was measured via a self-report symptom severity scale that was delivered at each visit as part of routine care. Symptoms included Anxiety, Depression, Irritability, Apathy, Fatigue, Body Pain, Insomnia, Headache, Psychosis, and Cognitive Disability were retrieved from the medical records. Besides individual scores ranging from 0-10 per symptom, a total score ranging (0-100) was calculated.

Besides self-report symptom severity, the National Institute of Health Toolbox measurements were used to collect composite-level outcomes in cognitive, emotional and psychosocial domains. These measures were chosen because they were designed specifically to provide valid, longitudinal assessment of neuropsychiatric symptoms in community-based populations for children, adults and elderly. Specifically, measurements were made using the NIH Toolbox Pattern Comparison Processing Speed and Dimensional Change Card Sort, General Life Satisfaction, Meaning and Purpose, and Social Satisfaction tests.

Visit & Treatment Group Designation

All patients were assigned a baseline visit and two follow-up visits. The baseline visit was assigned as the closest visit before which the patient started the treatment of interest. The first follow-up visit was the closest visit within approximately one month of starting the medication. The last follow-up visit was the last time point of observation on the treatment of interest. Three different treatments were compared: before and after telmisartan, before and after verapamil, and before and after combination treatment.

Medication Adherence

Medication adherence was confirmed by reviewing the medical record including pharmacy records of administration as well as physician notes.

Weber Lateralization

As part of routine care, the Weber test was delivered to patients during their initial and/or follow-up visits, depending on time availability in the clinic. The lateralization of the Weber was used for this study as a proxy of normalization of functional connectivity in the auditory functional network.

Statistics

A paired samples t-test was used to measure the significance of changes before and after treatment. Effect sizes were calculated using Cohen's methodology and quantified using standard ranges signifying small (0.2 to 0.5), medium (0.5 to 0.8) or large (above 0.8) effects of treatment. In addition, paired t-tests were used to compare outcomes between different doses of combination therapy. Subgroup analyses were performed for individuals with baseline clinical anxiety of moderate (4 and above), baseline clinical anxiety of severe (7 and above), baseline clinical cognitive disability of moderate (4 and above) and baseline cognitive disability of severe (7 and above). In a separate sensitivity analysis, all visits for patients, rather than only before and after visits, were used to calculate average symptom severity Off medication vs. On medication. To test the association between medication change and Weber lateralization, chi square analysis was performed. Treatment group was categorized as Change in Combination Treatment vs. No Change. Lateralization was rated as Left, Left Middle, Middle, Right Middle and Right. Data analysis was done using STATA (Stata/IC 16.1).

Other Embodiments

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A therapeutic combination for the treatment of a panic disorder, social anxiety disorder, or post-traumatic stress disorder in a subject in need thereof, the therapeutic combination comprising an effective amount of verapamil and telmisartan for the treatment of a panic disorder, social anxiety disorder, or post-traumatic stress disorder, wherein the effective amount of verapamil is between about 120 mg and 360 mg and the effective amount of telmisartan is between about 40 mg and about 180 mg, and wherein the mass ratio of verapamil to telmisartan in the combination is between about 2:1 and about 3:1.

2. The therapeutic combination of claim 1, wherein verapamil and telmisartan are formulated separately.

3. The therapeutic combination of claim 1, wherein verapamil and telmisartan are formulated together.

4. The therapeutic combination of claim 1, wherein verapamil and/or telmisartan is provided in an extended release formulation.

5. The therapeutic combination of claim 1, wherein the mass ratio of verapamil to telmisartan is about 3:1.

6. A therapeutic combination for the treatment of a panic disorder, social anxiety disorder, or post-traumatic stress disorder in a subject in need thereof, the therapeutic combination comprising an effective amount of verapamil and telmisartan for the treatment of a panic disorder, social anxiety disorder, or post-traumatic stress disorder, wherein the effective amount of verapamil is between about 120 mg and about 360 mg of, and the effective amount of telmisartan is between about 40 mg and about 180 mg of telmisartan, wherein the mass ratio of is about 3:1.

7. The therapeutic combination of claim 6, wherein the effective amount of verapamil is between about 250 and about 360 mg and the effective amount of telmisartan is at least 90 mg.

8. The therapeutic combination of claim 6, wherein the effective amount of verapamil is about 288 mg and the effective amount of telmisartan is about 96 mg.

9. The therapeutic combination of claim 6, wherein verapamil and telmisartan are formulated separately.

10. The therapeutic combination of claim 6, wherein verapamil and telmisartan are formulated together.

11. The therapeutic combination of claim 6, wherein verapamil and/or telmisartan is provided in an extended release formulation.

12. The therapeutic combination of claim 6, wherein verapamil and/or telmisartan is provided in an extended release formulation.

13. A therapeutic combination for the treatment of a panic disorder, social anxiety disorder, or post-traumatic stress disorder in a subject in need thereof, the therapeutic combination comprising an effective amount of verapamil and telmisartan for the treatment of a panic disorder, social anxiety disorder, or post-traumatic stress disorder, wherein the mass ratio of verapamil to telmisartan is about 3:1, the effective amount of verapamil is between about 250 mg and about 360 mg, and the effective amount of the telmisartan is between about 90 mg and about 180 mg.

14. The therapeutic combination of claim 13, wherein the effective amount of verapamil is about 288 mg and the effective amount of telmisartan is about 96 mg.

15. The therapeutic combination of claim 13, wherein the therapeutic combination consists of verapamil and telmisartan.

16. The therapeutic combination of claim 13, wherein the verapamil and/or telmisartan is provided in an extended release formulation.

17. The therapeutic combination of claim 13, wherein the verapamil is provided in an extended release formulation.

18. The therapeutic combination of claim 13, wherein the verapamil and telmisartan are formulated together.

19. The therapeutic combination of claim 13, wherein the effective amount of the verapamil is about 288 mg and the effective amount of the telmisartan is about 96 mg.

* * * * *